(12) United States Patent
Kouider et al.

(10) Patent No.: US 12,307,013 B2
(45) Date of Patent: May 20, 2025

(54) BRAIN-COMPUTER INTERFACE

(71) Applicant: NextMind SAS, Paris (FR)

(72) Inventors: Sid Kouider, Paris (FR); Robin Zerafa, Paris (FR); Nelson Steinmetz, Paris (FR); Nicolas Barascud, Paris (FR)

(73) Assignee: SNAP INC., Santa Monica, CA (US)

( * ) Notice: Subject to any disclaimer, the term of this patent is extended or adjusted under 35 U.S.C. 154(b) by 0 days.

(21) Appl. No.: 18/657,558

(22) Filed: May 7, 2024

(65) Prior Publication Data

US 2024/0295924 A1     Sep. 5, 2024

Related U.S. Application Data

(63) Continuation of application No. 17/758,471, filed as application No. PCT/EP2021/050393 on Jan. 11, 2021, now Pat. No. 11,995,236.

(60) Provisional application No. 62/958,072, filed on Jan. 7, 2020.

(51) Int. Cl.
*G06F 3/01* (2006.01)
*A61B 5/378* (2021.01)

(52) U.S. Cl.
CPC ............. *G06F 3/015* (2013.01); *G06F 3/013* (2013.01); *A61B 5/378* (2021.01)

(58) Field of Classification Search
CPC ............. G06F 3/011–015; G06F 3/01; A61B 5/367–383
See application file for complete search history.

(56) References Cited

U.S. PATENT DOCUMENTS

| 11,995,236 | B2 | 5/2024 | Kouider et al. |
| 2014/0058483 | A1 | 2/2014 | Zao et al. |
| 2019/0350510 | A1 | 11/2019 | Simpson |
| 2020/0337653 | A1* | 10/2020 | Alcaide ................. A61B 5/369 |
| 2023/0032492 | A1 | 2/2023 | Kouider et al. |

FOREIGN PATENT DOCUMENTS

| CN | 114981759 A | 8/2022 |
| CN | 114981759 | 12/2024 |
| WO | WO-2019144019 A1 | 7/2019 |
| WO | WO-2021140247 A1 | 7/2021 |

OTHER PUBLICATIONS

"U.S. Appl. No. 17/758,471, Non Final Office Action mailed Aug. 15, 2023", 14 pgs.

(Continued)

*Primary Examiner* — Lisa S Landis
(74) *Attorney, Agent, or Firm* — SCHWEGMAN LUNDBERG & WOESSNER, P.A.

(57) ABSTRACT

A system and method relating to a brain-computer interface in which a visual stimulus overlaying one or more objects is provided, the visual stimulus having a characteristic modulation. The brain computer interface measures neural response to objects viewed by a user. The neural response to the visual stimulus is correlated to the modulation. The method allows the interface to discriminate between merely viewing of a display object and deliberate selection of that display object (for example, as a trigger to a further action).

20 Claims, 14 Drawing Sheets

(56) References Cited

OTHER PUBLICATIONS

"U.S. Appl. No. 17/758,471, Notice of Allowance mailed Jan. 23, 2024", 7 pgs.
"U.S. Appl. No. 17/758,471, Response filed Nov. 15, 2023 to Non Final Office Action mailed Aug. 15, 2023", 11 pgs.
"Chinese Application Serial No. 202180009809.9, Voluntary Amendment Filed Dec. 19, 2022", w/ English Claims, 10 pgs.
"International Application Serial No. PCT/EP2021/050393, International Search Report mailed Apr. 6, 2021", 5 pgs.
"International Application Serial No. PCT/EP2021/050393, Written Opinion mailed Apr. 6, 2021", 8 pgs.
Kenemans, J L, et al., "On the processing of spatial frequencies as revealed by evoked-potential source modeling", Clinical Neurophysiology, Elsevier Science, IE, vol. III, No. 6, (May 26, 2017), 1113-1123.
Kian, B Ng, et al., "Paper;Stimulus specificity of a steady-state visual-evoked potential-based brain computer interface", Journal of Neural Engineering, Institute of Physics Publishing, Bristol, GB, vol. 9, No. 3, (May 15, 2012), 36008.
"Korean Application Serial No. 10-2022-7027050, Notice of Preliminary Rejection mailed Sep. 20, 2024", w/ English Translation, 14 pgs.
"European Application Serial No. 21700292.2, Response to Communication Pursuant to Rules 161 and 162 EPC Filed Feb. 16, 2023", 23 pgs.
"Korean Application Serial No. 10-2022-7027050, Response filed Nov. 19, 2024 to Notice of Preliminary Rejection mailed Sep. 20, 2024", W English Claims, 18 pgs.
"European Application Serial No. 24204491.5, Extended European Search Report mailed Jan. 7, 2025", 11 pgs.

\* cited by examiner (c)

(d)

BRAIN-COMPUTER INTERFACE

CROSS-REFERENCE TO RELATED APPLICATIONS

This application is a continuation of U.S. patent application Ser. No. 17/758,471, filed on Jul. 7, 2022, which is a U.S. national-phase application filed under 35 U.S.C. § 371 from International Application Serial No. PCT/EP2021/050393, filed Jan. 11, 2021, and published as WO 2021/140247 on Jul. 15, 2021, which claims the benefit of priority to U.S. Provisional Application Ser. No. 62/958,072, filed Jan. 7, 2020, each of which are incorporated herein by reference in their entireties.

TECHNICAL FIELD OF THE INVENTION

Embodiments of the present disclosure relate to differentiation between exploration and selection in brain-computer interfaces involving visual sensing.

STATE OF THE ART

In visual brain-computer interfaces (BCIs), neural responses to a target stimulus, generally among a plurality of generated visual stimuli presented to the user, are used to infer (or "decode") which stimulus is essentially the object of focus at any given time. The object of focus can then be associated with a user-selectable or -controllable action.

Neural responses may be obtained using a variety of known techniques. One convenient method relies upon surface electroencephalography (EEG), which is non-invasive, has fine-grained temporal resolution and is based on well-understood empirical foundations. Surface EEG makes it possible to measure the variations of diffuse electric potentials on the surface of the skull (i.e. the scalp) of a subject in real-time. These variations of electrical potentials are commonly referred to as electroencephalographic signals or EEG signals.

In a typical BCI, visual stimuli are presented in a display generated by a display device. Examples of suitable display devices (some of which are illustrated in FIG. 3) include television screens & computer monitors 302, projectors 310, virtual reality headsets 306, interactive whiteboards, and the display screen of tablets 304, smartphones, smart glasses 308, etc. The visual stimuli 311, 311', 312, 312', 314, 314', 316 may form part of a generated graphical user interface (GUI) or they may be presented as augmented reality (AR) or mixed reality graphical objects 316 overlaying a base image: this base image may simply be the actual field of view of the user (as in the case of a mixed reality display function projected onto the otherwise transparent display of a set of smart glasses) or a digital image corresponding to the user's field of view but captured in real-time by an optical capture device (which may in turn capture an image corresponding to the user's field of view amongst other possible views).

Inferring which of a plurality of visual stimuli (if any) is the object of focus at any given time is fraught with difficulty. For example, when a user is facing multiple stimuli, such as for instance the digits displayed on an on-screen keypad (see FIG. 4), it has proven very difficult to infer which one is under focus directly from brain activity at a given time. The user perceives the digit under focus, say digit 5, so the brain must contain information that distinguishes that digit from others, but current methods are unable to extract that information. That is, current methods can infer that a stimulus has been perceived, but they cannot determine which specific stimulus is under focus using brain activity alone.

To overcome this issue and to provide sufficient contrast between stimulus and background (and between stimuli), it is known to configure the stimuli used by visual BCIs to blink or pulse (e.g. large surfaces of pixels switching from black to white and vice-versa), so that each stimulus has a distinguishable characteristic profile over time. The flickering stimuli give rise to measurable electrical responses. Specific techniques monitor different electrical responses, for example steady state visual evoked potentials (SSVEPs) and P-300 event related potentials. In typical implementations, the stimuli flicker at a rate exceeding 6 Hz. As a result, such visual BCIs rely on an approach that consists of displaying, in a display device, the various stimuli discretely rather than constantly, and at typically at different points in time. Brain activity associated with attention focused on a given stimulus is found to correspond (i.e. correlate) with one or more aspect of the temporal profile of that stimulus, for instance the frequency of the stimulus blink and/or the duty cycle over which the stimulus alternates between a blinking state and a quiescent state.

Thus, decoding of neural signals relies on the fact that when a stimulus is turned on (i.e. presented), it will trigger a characteristic pattern of neural responses in the brain that can be determined from electrical signals, i.e. the SSVEPs or P-300 potentials, picked up by electrodes of an EEG device, the electrodes of an EEG helmet, for example. Continuing with the keypad example illustrated in FIG. 4, this neural data pattern might be very similar or even identical for the various digits, but it is time-locked to the digit being perceived: only one digit may pulse at any one time so that the correlation with a pulsed neural response and a time at which that digit pulses may be determined as an indication that that digit is the object of focus. By displaying each digit at different points in time, turning that digit on and off at different rates, applying different duty cycles, and/or simply applying the stimulus at different points in time, the BCI algorithm can establish which stimulus, when turned on, is most likely to be triggering a given neural response, thereby allowing a system to determine the target under focus.

Even after target is determined to be in focus, visual computer interfaces such as the BCI described above face further challenges. One major challenge in the field of visual computer interfaces is the so-called "Midas Touch" Problem, where the user inadvertently generates an output action when simply looking at a target stimulus (the stimulus may be anywhere in the user's field of view 404 including the focal area 418) without ever intending to trigger the related action. Indeed, it has proven difficult to estimate accurately whether a viewed target is only "explored" or whether the user also wishes to select that target (i.e. to generate an output action).

In the field of eye-tracking, the Midas Touch Problem reflects the difficulty in estimating whether the user is fixing their gaze a particular target for exploration or deliberately (for "selection" of that target and/or for generating an output action on the interface). This estimation is usually done by measuring dwell time: a timer is started when the (tracked) gaze enters a target area and is validated when the timer elapses (without significant divergence of gaze). Dwell time can be extremely frustrating to work with as it relies on a user's observation to infer interaction. Although eye-tracking information are used reliably to reveal the user's gaze location, it has proven difficult to offer intentional control to the user, due to the inability to discriminate between mere observation of the (gazed-at) target by the user (i.e. exploration) and deliberate staring intended to express the user's will to trigger an action associated with the target.

While the Midas Touch Problem is a major challenge in the field of eye-tracking based user interface, it also arises in visual BCIs. The user may wish to investigate (i.e. pay attention to) a display object without ever meaning to control the object or trigger an associated action. Moreover, there are circumstances where the user of a BCI allows their gaze to linger on a screen object exhibiting a (decodable) visual stimulus with no associated attention—e.g. in a blank (or vacant) stare. It is desirable to discriminate such cases from cases where control or triggered action is intended.

Consequently, there is a need for an improved method for operating a BCI to discriminate between a target upon which a user is focusing with the intention of triggering an action and a screen object that is merely being looked at (whether inadvertently or with intention only to investigate). It is therefore desirable to provide brain-computer interfaces that address the above challenges.

SUMMARY

The present disclosure relates to a brain-computer interface (BCI) in which a display object or an overlay object overlaying one or more display objects exhibits a compound visual stimulus. The compound visual stimulus is generated by a stimulus generator and typically presented on a screen or other display device. The compound visual stimulus comprises at least a first portion and a second portion. In certain embodiments, the first and second portions of the stimulus may be presented as overlapping the same display location (as illustrated in FIG. 7A (b) where the first stimulus portion consists of "ticks" and the second portion of "crosses").

The first portion of the compound visual stimulus has a first characteristic modulation, while the second portion of the compound visual stimulus has a second characteristic modulation, the second characteristic modulation being distinct from the first characteristic modulation. Neural responses to the objects in the user's field of view are captured by a neural signal capture device in the BCI. The user's neural response to the viewed objects (and their associated characteristic modulations) may in turn be measured and decoded to determine which object of interest is the focus of the user's attention.

Where the display object or overlay object is merely viewed, the neural response is evenly distributed between first and second portions of the compound visual stimulus. The user is able to discriminate consciously between the portions by virtue of a visual property of the respective portions. For example, the first portion may be presented in a first color (green, say) while the second portion is presented in a second, different, color (red, say). Where the user deliberately focusses attention on one of the first and second portions (the one displayed in green, for instance), the neural response becomes stronger for the portion having the attended visual property and the BCI may infer that deliberate attention is associated with the viewed object.

According to a first aspect, the present disclosure relates to a brain computer interface system, comprising: a display unit for displaying image data, the image data including at least one object, the display unit further outputting a respective visual stimulus to correspond to one or more of said objects, a stimulus generator for generating the or each visual stimulus with a corresponding characteristic modulation; a neural signal capture device configured to capture neural signals associated with a user; and an interfacing device operatively coupled to the neural signal capture device and the stimulus generator, the interfacing device being configured to: receive the neural signals from the neural signal capture device; determine a strength of components of the neural signals having a property associated with the respective characteristic modulations of the or each visual stimulus; determine which of the at least one visual stimuli is associated with an object of focus of the user based on the neural signals, the object of focus being inferred from the presence and/or relative strength of the components of the neural signals having a property associated with the characteristic modulation of the visual stimulus; and cause the stimulus generator to generate the visual stimulus as a compound visual stimulus comprising at least a first portion with a first characteristic modulation and a first visual property and a second portion with a second characteristic modulation and a second visual property, the second visual property being distinct from the first visual property. In certain embodiments, the second visual property is orthogonal to the first visual property, each property being perceived and decodable independently of the other.

According to a second aspect, the present disclosure relates to a method of operation of a brain computer interface system, the brain computer interface system including a display unit, a stimulus generator and a neural signal capture device, the display unit displaying image data including at least one object and outputting a visual stimulus to correspond to one or more of said objects, the visual stimulus having a characteristic modulation, wherein the method comprises, in a hardware interfacing device operatively coupled to the neural signal capture device and the stimulus generator: receiving the neural signals from the neural signal capture device; determining a strength of components of the neural signals having a property associated with the respective characteristic modulations of the or each visual stimulus; determining which of the at least one visual stimuli is associated with an object of focus of the user based on the neural signals, the object of focus being inferred from the presence and/or relative strength of the components of the neural signals having a property associated with the characteristic modulation of the visual stimulus; and causing the stimulus generator to generate the visual stimulus as a compound visual stimulus comprising at least a first portion with a first characteristic modulation and a first visual property and a second portion with a second characteristic modulation and a second visual property, the second visual property being distinct from the first visual property.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

The description that follows includes systems, methods, techniques, instruction sequences, and computing machine program products that embody illustrative embodiments of the disclosure. In the following description, for the purposes of explanation, numerous specific details are set forth in order to provide an understanding of various embodiments of the inventive subject matter. It will be evident, however, to those skilled in the art, that embodiments of the inventive subject matter may be practiced without these specific details. In general, well-known instruction instances, protocols, structures, and techniques are not necessarily shown in detail.

Figure 1:
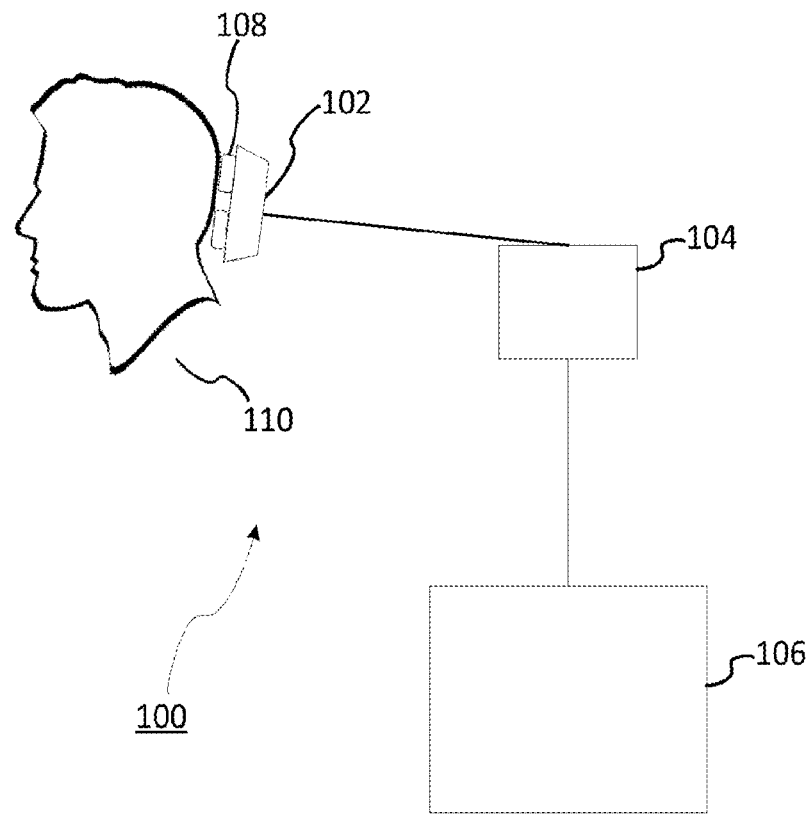
FIG. 1 illustrates an electronic architecture for receiving and processing EEG signals according to the present disclosure.

FIG. 1 illustrates an example of an electronic architecture for the reception and processing of EEG signals by means of an EEG device 100 according to the present disclosure.

To measure diffuse electric potentials on the surface of the skull of a subject 110, the EEG device 100 includes a portable device 102 (i.e. a cap or headpiece), analog-digital conversion (ADC) circuitry 104 and a microcontroller 106. The portable device 102 of FIG. 1 includes one or more electrodes 108, typically between 1 and 128 electrodes, advantageously between 2 and 64, advantageously between 4 and 16.

Each electrode 108 may comprise a sensor for detecting the electrical signals generated by the neuronal activity of the subject and an electronic circuit for pre-processing (e.g. filtering and/or amplifying) the detected signal before analog-digital conversion: such electrodes being termed "active". The active electrodes 108 are shown in use in FIG. 1, where the sensor is in physical contact with the subject's scalp. The electrodes may be suitable for use with a conductive gel or other conductive liquid (termed "wet" electrodes) or without such liquids (i.e. "dry" electrodes).

Each ADC circuit 104 is configured to convert the signals of a given number of active electrodes 108, for example between 1 and 128.

The ADC circuits 104 are controlled by the microcontroller 106 and communicate with it for example by the protocol SPI ("Serial Peripheral Interface"). The microcontroller 106 packages the received data for transmission to an external processing unit (not shown), for example a computer, a mobile phone, a virtual reality headset, an automotive or aeronautical computer system, for example a car computer or a computer system. airplane, for example by Bluetooth, Wi-Fi ("Wireless Fidelity") or Li-Fi ("Light Fidelity").

In certain embodiments, each active electrode 108 is powered by a battery (not shown in FIG. 1). The battery is conveniently provided in a housing of the portable device 102.

In certain embodiments, each active electrode 108 measures a respective electric potential value from which the potential measured by a reference electrode (Ei=Vi−Vref) is subtracted, and this difference value is digitized by means of the ADC circuit 104 then transmitted by the microcontroller 106.

In certain embodiments, the method of the present disclosure introduces target objects for display in a graphical user interface of a display device. The target objects include control items and the control items are in turn associated with user-selectable actions.

Figure 2:
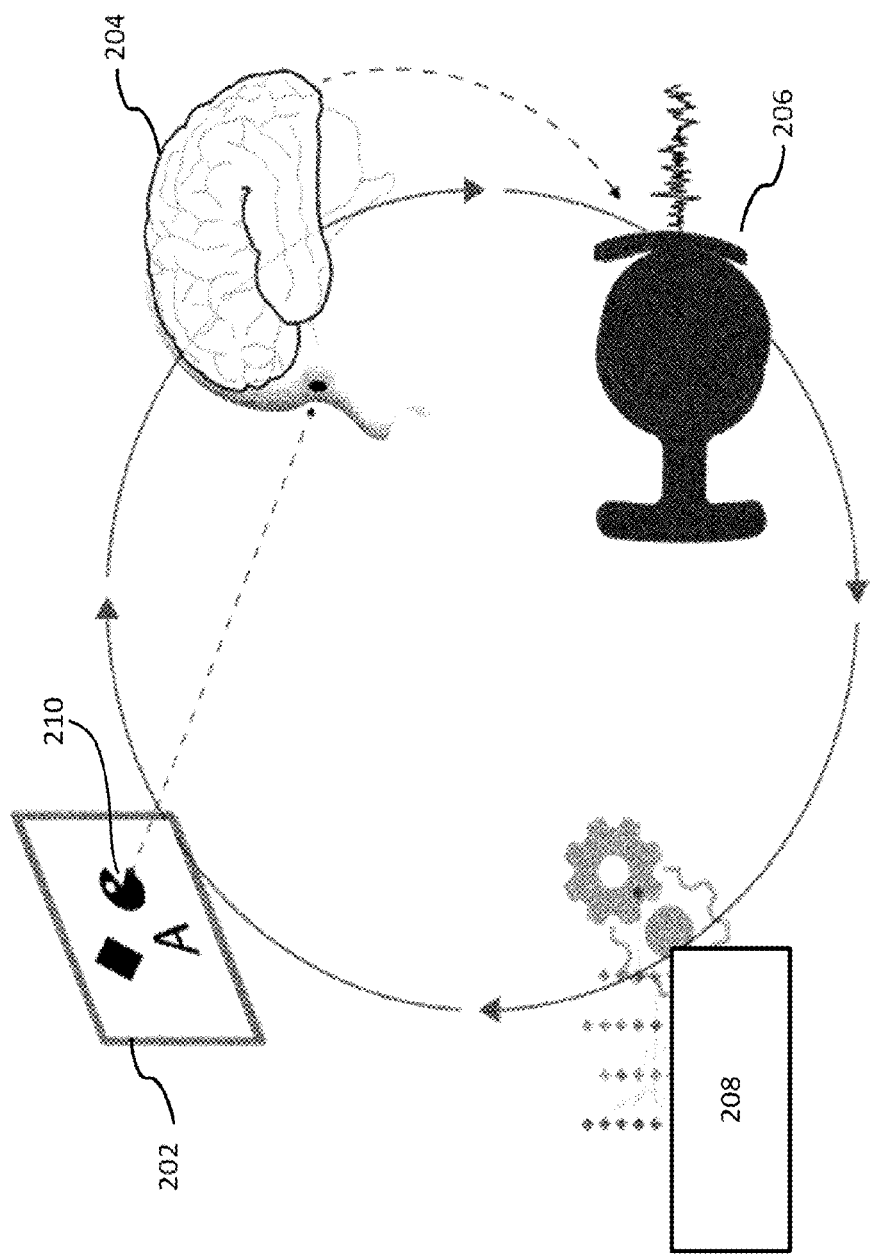
FIG. 2 illustrates a system incorporating a brain computer interface (BCI) according to the present disclosure.
Figure 3:
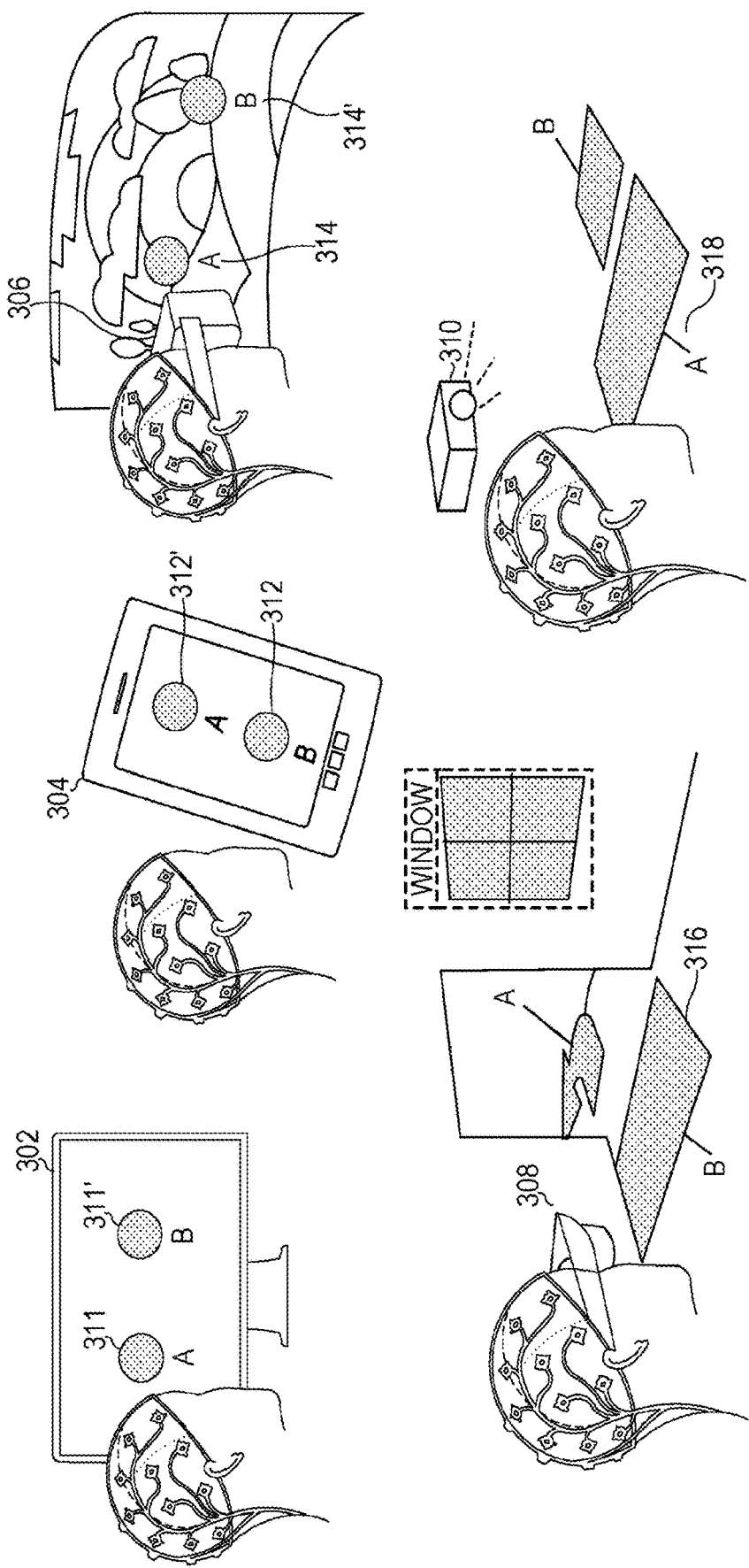
FIG. 3 illustrates various examples of display device suitable for use with the BCI system of the present disclosure.

FIG. 2 illustrates a system incorporating a brain computer interface (BCI) according to the present disclosure. The system incorporates a neural response device 206, such as the EEG device 100 illustrated in FIG. 1. In the system, an image is displayed on a display of a display device 202. The subject 204 views the image on the display, focusing on a target object 210.

In an embodiment, the display device 202 displays at least the target object 210 as a graphical object with a varying temporal characteristic distinct from the temporal characteristic of other displayed objects and/or the background in the display. The varying temporal characteristic may be, for example, a constant or time-locked flickering effect altering the appearance of the target object at a rate greater than 6 Hz. In another embodiment, the varying temporal characteristic may use a pseudo-random temporal code so that a flickering effect is generated that alters the appearance of the target object a few times a second on average, for example at a rate that is on average 3 Hz. Where more than one graphical object is a potential target object (i.e. where the viewing subject is offered a choice of target object to focus attention on), each object is associated with a discrete spatial and/or temporal code.

The neural response device 206 detects neural responses (i.e. tiny electrical potentials indicative of brain activity in the visual cortex) associated with attention focused on the target object; the visual perception of the varying temporal characteristic of the target object(s) therefore acts as a stimulus in the subject's brain, generating a specific brain response that accords with the code associated with the target object in attention. The detected neural responses (e.g. electrical potentials) are then converted into digital signals and transferred to a processing device 208 for decoding. Examples of neural responses include visual evoked potentials (VEPs), which are commonly used in neuroscience research. The term VEPs encompasses conventional SSVEPs, as mentioned above, where stimuli oscillate at a specific frequency and other methods such as the code-modulated VEP, stimuli are subject to a variable or pseudo-random temporal code. The neural response, where the brain appears to "oscillate" or respond in synchrony with the flickering temporal characteristic is referred to herein as "neurosynchrony".

The processing device 208 executes instructions that interpret the received neural signals to determine feedback indicating the target object having the current focus of (visual) attention in real-time. Decoding the information in the neural response signals relies upon a correspondence between that information and one or more aspect of the temporal profile of the target object (i.e. the stimulus). In certain embodiments, the processing device 208 and neural response device 206 may be provided in a single device so that decoding algorithms are executed directly on the detected neural responses.

In certain embodiments, the processing device may conveniently generate the image data presented on the display device 202 including the temporally varying target object.

In certain embodiments, the display device 202 displays an overlay object as a graphical object with a varying temporal characteristic distinct from the temporal characteristic of other displayed objects and/or the background in the display, the overlay object is then displayed as a graphical layer over at least an identified target object.

Although neural activity to external stimuli can be modulated by top-down voluntary attention, stimulus reconstruction is also in large part driven by bottom-up factors that will automatically affect neural oscillations for the observed target regardless of attention, rendering difficult the estimation of whether or not an action is intended by the user.

To address this difficulty, an embodiment of the present disclosure presents a compound visual stimulus for each target: instead of a single visual stimulus, the compound visual stimulus comprises at least two stimulus portions with distinct neural signatures. In certain embodiments, these two stimulus portions are overlaid at substantially the same location, each with a distinct temporal modulation pattern. One portion is used for validation (i.e. to allow the BCI to infer deliberate attention) and the other portion for balancing the bottom-up impact of the validation stimulus: deliberately attending to one stimulus portion (at the expense of the other) for the purpose of triggering an action has a different neurosynchrony pattern from merely viewing the target without distinguishing the portions. The principle behind this approach is that the user attending a given display object (e.g. a letter 'A') merely for exploration would not select it until they focus specifically on a given overlaid portion, say green lines ("validating stimulus") rather than red line ("balancing stimulus").

Research in cognitive neuroscience on the cortical modulations of feature-based attention reveals that is possible to distinguish neural signatures between two sets of flickering points displayed at the same location, such as one displayed in green at a specific frequency (e.g., 8 Hz) and another in red at another frequency (e.g., 9 Hz). That is, a peak in the two corresponding frequencies can be observed in spectral representations of the neural data. Moreover, if the subject is asked to preferentially attend to one specific stimulus, such as the green points, and ignore the alternative, red, stimulus, the neural response at the frequency of the attended stimulus (8 Hz) will increase, while the neural response at the frequency of the ignored stimulus (9 Hz) will decrease compared to a baseline.

In certain embodiments this observation is applied to BCIs. As a result, feature-based attention may be used to offer real-time volitional control over selecting a target for triggering a corresponding output action. By overlaying two stimulus portions with distinct neural signatures at the same location on a given target (i.e. display object), such as for instance green points at 8 Hz and red points at 9 Hz on top of the letter A, the user is offered the possibility of exploring letter A without selection, and then selecting the letter for an action by preferentially attending to the green points on the letter. In certain cases, the display object is a compound visual stimulus of two collocated stimulus portions.

Consider the case where green dots are the validating stimulus portion, and red dots are the balancing stimulus portion. In such examples, merely observing a target (e.g. a letter 'A') will lead to bottom-up (automatic) neural amplification in both frequencies associated with the validation stimulus and the balancing stimulus, in a way that can be interpreted as a balanced, unbiased neural responses merely reflecting exploration of the target. This is because the balanced stimulus is used to counterbalance the bottom-up (automatic) neural impact of the validation stimulus.

However, when the user intentionally attends the validating (e.g. green) stimulus portion, neural amplification at the corresponding frequency may be interpreted as volitional control to trigger an action.

In other examples, the general approach of the present disclosure may be extended to any situation in which a validating stimulus is used in conjunction with one or more balancing stimuli with distinctive neural signatures, whether it is based on temporal, spectral, spatial or any other characteristics of neural data. Thus, the distinction between the stimuli through which the user may indicate intention need not be color: one alternative visible property would be rate or orientation of movement of visual elements, for instance.

In another alternative, an overlay of green lines and an overlay of red lines may be presented superimposed on the letter A, both oscillating at a common frequency (8 Hz, say) but in phase opposition. The same principle is applied on the letter B at 9 Hz. The analysis of neural responses would reveal whether the user is exploring letter A (stronger neural oscillation at 8 Hz) or letter B (stronger neural oscillation at 9 Hz). This frequency analysis may be coupled with an analysis of the phase of neural responses to determine whether the user is just exploring (i.e. investigating) one of the letters or intending to validate it by focusing on the green colored overlay.

It is noted that, in the above example, the overlaid stimulus portions have characteristic modulations that differ only in phase and not in frequency.

An important aspect to take into consideration is the fact that neural responses (as measured by EEG devices) are prone to non-linearities, so when the user is visually exploring displayed objects rather than actively seeking to select one object (i.e. when gazing at letter A without exhibiting a preference for the validating stimulus over the balancing stimulus) the impact of the two stimulus portions is not necessarily additive. This is the case whether stimulus reconstruction or spectral analysis is used to decode the neural responses.

For spectral analysis, there is a well-known phenomenon called intermodulation. The term intermodulation refers to any sum of the non-zero integer-multiples of the fundamental frequencies (i.e. $n*f_1+m*f_2$, where n, m=−1, −2, −3, . . . ). Intermodulation components occur as a result of non-linear interaction between fundamental frequencies. It is possible, for instance, to have a case where attention is paid to a location between two closely placed display objects (modulated, say, at respective frequencies $f_1$ at 8 Hz and $f_2$ at 9 Hz), with letter "A" on the left side of the location and letter "B" on the right side at the same time (so-called "dual covert attention"). In such a case, a spectral analysis will reveal power increase at both 8 and 9 Hz, but also on their intermodulation components such as ($f_2-f_1$: 1 Hz) and sum ($f_1+f_2$: 17 Hz). The magnitude, or presence vs. absence, of intermodulation components can provide information about whether the user is receiving information from both stimulus portions or preferentially attending one of them.

Successful identification of the attended stimulus may rely upon the assumption that the (stimulus) reconstruction is stronger for the validating stimulus compared to the balancing stimulus by reconstructing both and comparing them. To address non-additive neural responses, however, certain embodiments build on the use of more than one decoding model. In one such embodiment, two models are built that correspond respectively to paying attention to two stimuli vs. one stimulus; 'paying attention to two stimuli' may mean that the user is 'defocused' or attending the underlying object but not the distinctive elements of either stimulus. In another such embodiment, two models are separately trained on and for each stimulus. These embodiments can help distinguish between the cases where a user focuses on both stimuli vs. none (e.g. during "gazing"), or one stimulus vs. the other stimulus (e.g. during "exploration validation" or "selection validation"). As the different stimuli can have distinct impacts upon neural responses, both qualitatively (they may generate different VEPs waveforms) and quantitatively (particular stimuli may give rise to a weaker response amplitude in the brain than others), it may be a challenge to fully balance validation and balancing stimuli when using only a single decoding model. By adopting more than one model, it becomes possible to account (and compensate) for neural response specificity and response bias.

As noted above, the present disclosure is not limited to color differentiated stimulus portions but may extend to any distinctive visual features. Instead of using green and red overlapping stimulus portions, one can use distinct movement directions (e.g. component elements of each stimulus portion moving coherently (i.e. "drifting") in respective different directions, upward vs. downward say, while occupying the same region of the display), distinct spatial frequencies, contrast, etc. Additionally or alternatively, one can provide visual distinction by adopting component elements of respective stimulus portions with different orientations (not just direction of movement, such as horizontal vs. vertical bars), and/or shapes (for instance, one or more small circles vs. one or more small triangle overlapping at a center or over an object). Different distinctive visual properties may, naturally, be used in combination. In addition, in certain embodiments, respective stimulus portions may adopt different modes of visual differentiation from one another: thus, the visual property in a first stimulus portion may be said to be 'orthogonal' to another visual property in a second stimulus portion in that each property is perceived and decodable independently of the other. So that two stimulus portions may appear totally different. Consider, for instance, a case where one stimulus portion adopts coherently colored, lenticular-shaped component elements while another stimulus portion adopts none of these modes of differentiation and appears as a patch of visual noise.

Figure 5A:
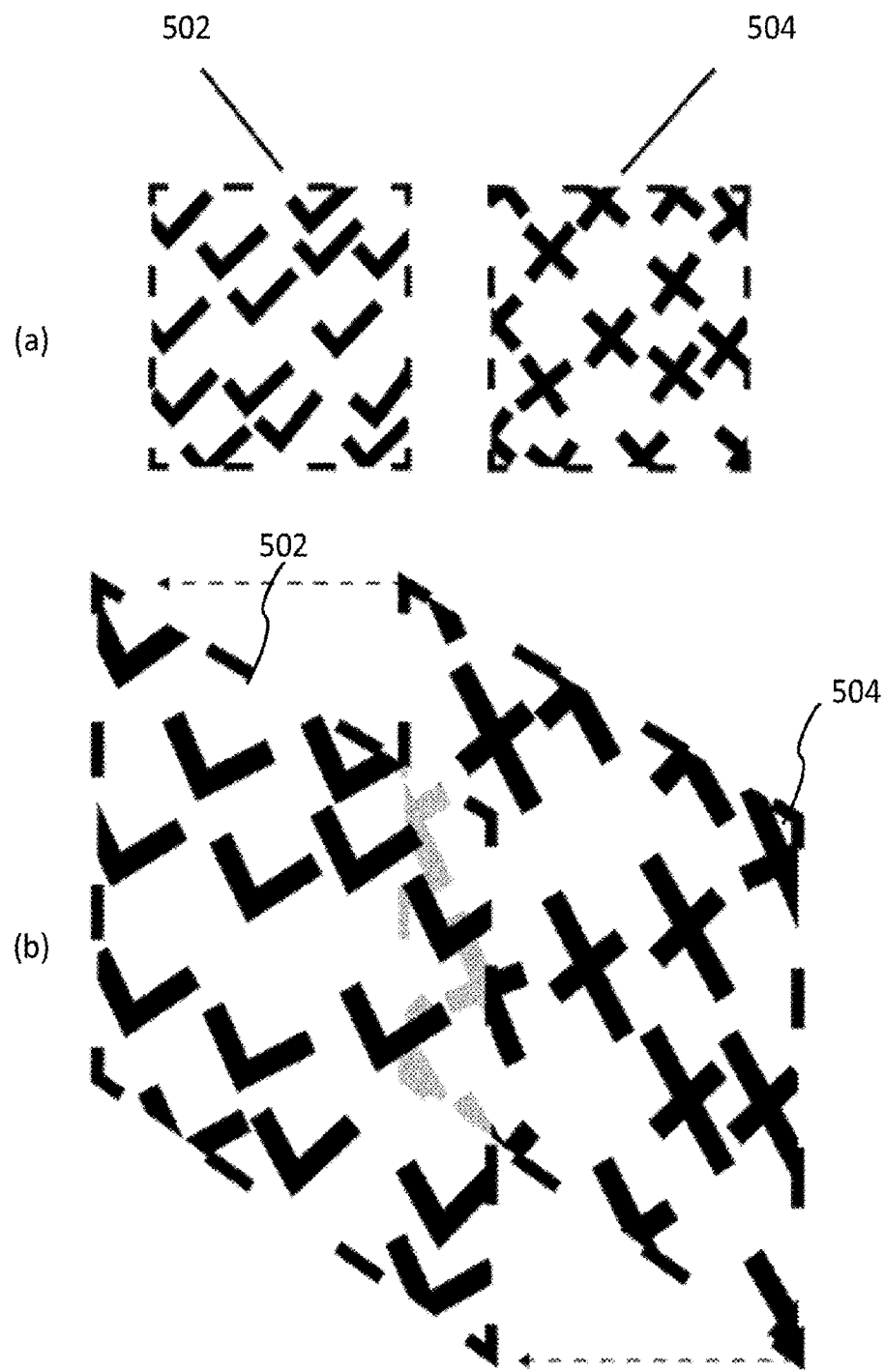
FIGS. 5A and 5B illustrate respective exemplary embodiments of compound visual stimulus in accordance with the present disclosure.

FIG. 5A illustrates an exemplary embodiment of compound visual stimulus in accordance with the present disclosure. Respective portions 502, 504 of a compound visual stimulus are shown in (a), each having a respective distinct varying characteristic modulation. These stimulus portions may be generated as distinct visual stimuli but the BCI causes them to be displayed at least partly overlapping one another. While respective portions may be visually distinguished by the user by color, they may additionally or alternatively be distinguished by the shape and orientation of stimuli component elements (as described above). For the sake of illustration, the compound visual stimulus shown in FIG. 5A comprises one portion having 'tick' symbols as a component element while the other portion has "cross" symbols. In accordance with the present disclosure the first portion, the "tick" portion 502, say, may be considered as a "validating stimulus" and the second portion, the "cross" portion 504, say, may be considered as a "balancing stimulus". The user concentrating on the ticks of the validating stimulus 502 results in a neural response that favors the validation of the selection of a display object under the compound visual stimulus.

Figure 5B:
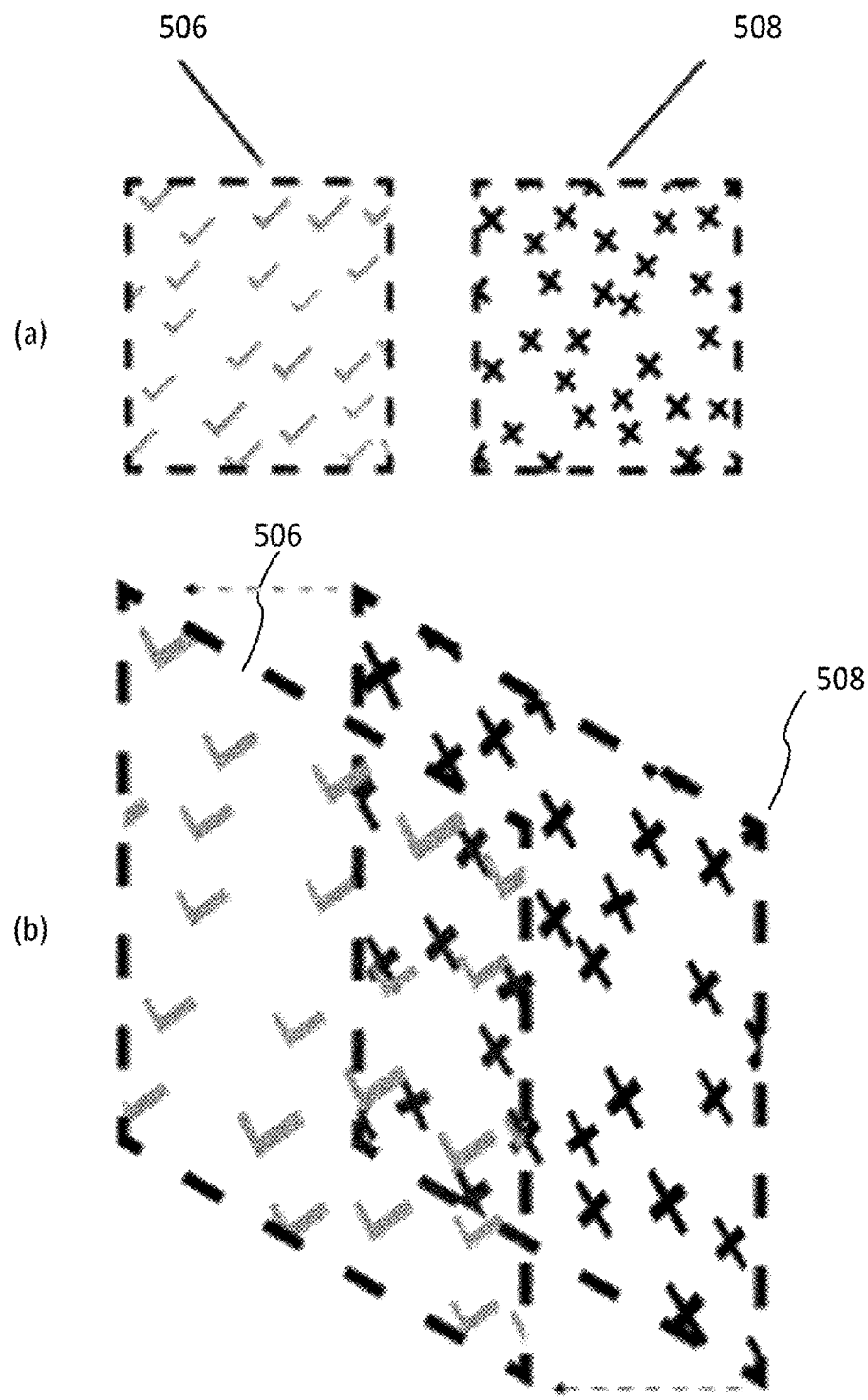

FIG. 5B illustrates a further exemplary embodiment of compound visual stimulus in accordance with the present disclosure. Respective portions 506, 508 of a compound visual stimulus are shown in (a), each having a respective distinct varying characteristic modulation. In this example, the shading of the "tick" portion 506 is lighter than that of the "cross" portion 508, illustrating the combination of visual properties (color/shade, as well as distinctive constituent visual elements).

The validation and balancing stimulus portions of the compound visual stimulus need not entail strong modulations but should induce equivalent response amplitudes such as to balance each other when one of them is not preferentially attended by the user. Normalization procedures could be used if the two categories are, regardless of attention, biased one way or another (e.g., when the validating stimulus has more strength than the other, due to salience, preference, familiarity, training, etc.). Indeed, as discussed below, it is noted that the selective application of characteristic modulations to the high spatial frequency (HSF) component of the visual stimulus portions may reduce discomfort and mental fatigue without significantly detracting from the strength of neural response.

Figure 6:
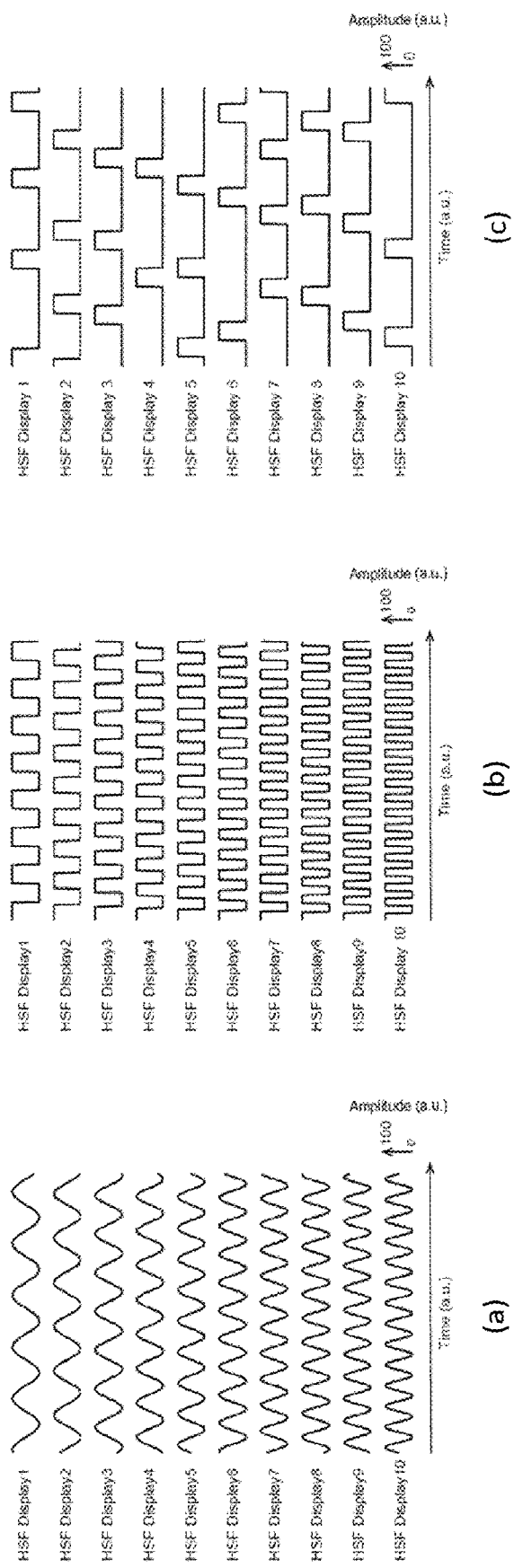
FIG. 6 illustrate different types of characteristic modulations applied to respective visual stimuli in accordance with the present disclosure.

FIG. 6 illustrates three different types of characteristic modulations (for the HSF component of respective pluralities of displayed visual stimuli). At (a), each of a first plurality of different visual stimuli has a respective sinusoidal characteristic modulation of different frequency (but a normalized peak amplitude). At (b), the characteristic modulations are again of different frequency and have a normalized peak amplitude but the modulation is a square wave. At (c), the characteristic modulations are instead minimally correlated signals with normalized peak amplitudes. In each case, the respective different stimuli may be applied to different display objects and/or (in pairs) to the same display object to provide a validation stimulus and a balancing stimulus for that display object.

The method of presenting stimulus portions of a compound visual stimulus at the same location described in the present disclosure allows the BCI to capture the attentional selection of one among two or more stimuli displayed at the same location, and allows the BCI to provide any desired form of feedback or action based on the stimulus.

The feedback could be a modification of the stimulus itself (for instance, visually highlighting or enlarging etc. a display object itself or the visual stimulus overlaying the display object) or it may be an action associated either symbolically or arbitrarily with the selected stimulus. For instance, with an overlay of two arrows pointing in opposite directions, one in green and the other in red, attentional selection of one arrow would lead to a corresponding movement in direction in the virtual reality environment. This feedback provides a positive feedback loop ("neurofeedback" loop) which takes place when the user is presented with a visual representation of his real-time correlations for the attended targets. The user's reinforced focus from the conscious intention of e.g. 'selecting a target', enhances the signal-to-noise-ratio of the response to the stimuli resulting in the positive feedback loop.

In co-pending International patent application number PCT/EP2020/081338 filed on Nov. 6, 2020, the entire specification of which is incorporated herein by reference, the authors describe an approach to feedback interaction, in which the user is presented with a visual feedback element that exhibits an effect which corresponds to their attention level. Such a feedback interaction may be used in conjunction with the presently disclosed operation. Thus, for example, the user would receive feedback and even a first validation (i.e. confirmation or "exploration validation") that the BCI had decoded (i.e. determined) that they are staring (or looking) at letter A, but the second validation (i.e. "selection validation") would only occur when green overlays are preferentially attended over red overlays. Feedback may be continuous until validation of a selection is achieved.

Figure 7A:
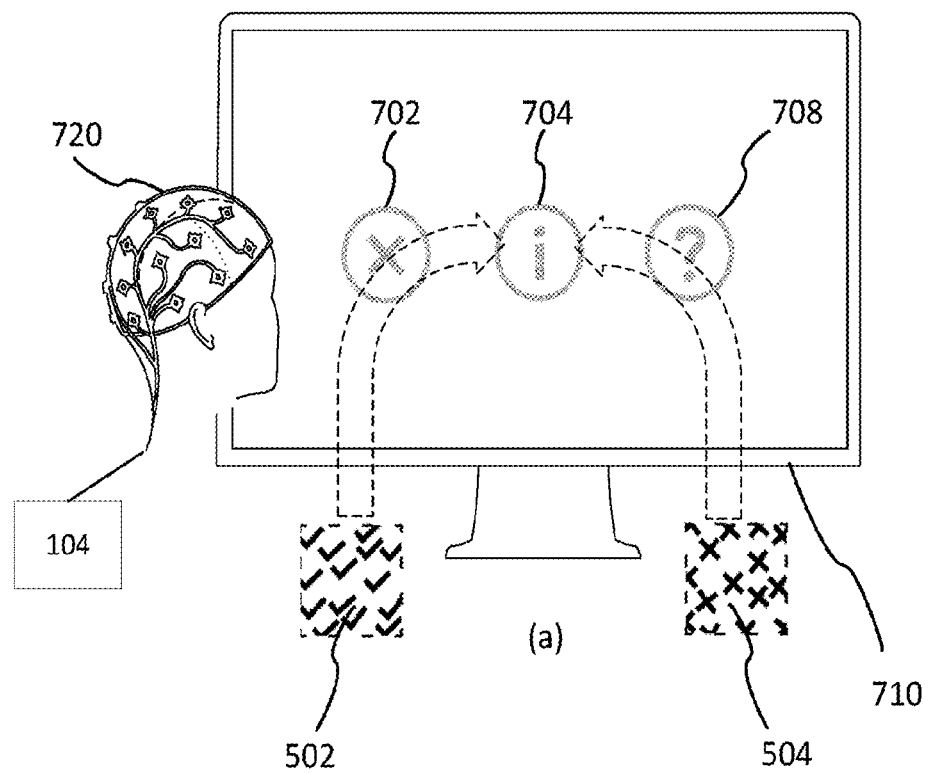
FIGS. 7A and 7B illustrate the progression from exploration to validated selection in the method of operation of the BCI in accordance with the present disclosure.
Figure 7A:
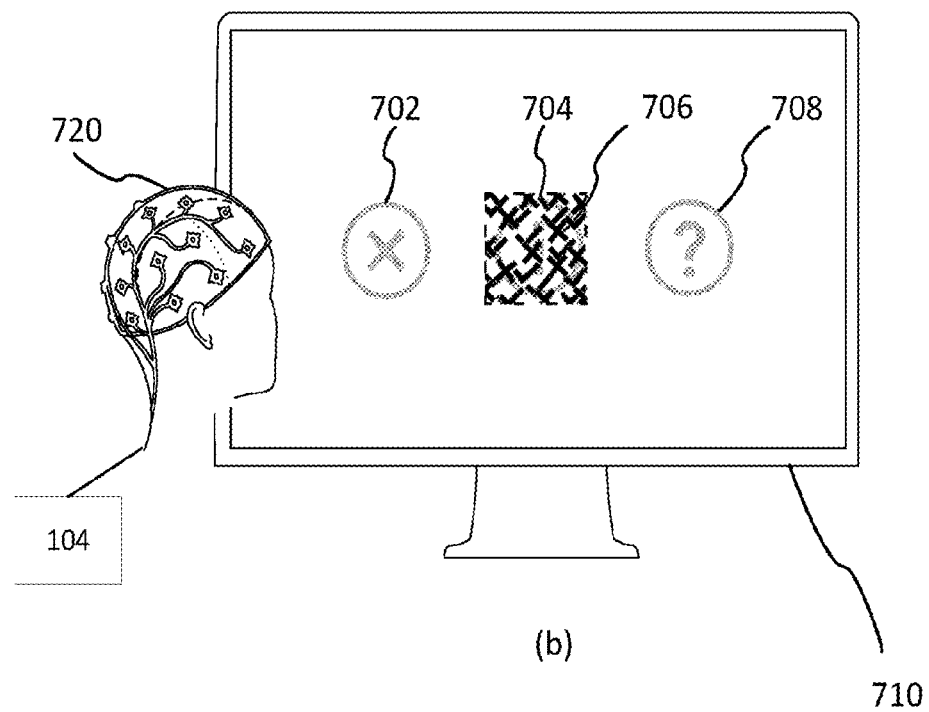

FIG. 7A illustrates the user experience of a display device 710 displaying a display object 704. In (a), a compound visual stimulus 706 (such as that illustrated in FIG. 5A) comprising a tick portion 502 and a cross portion 504 is generated and overlaid over the display object 704. Each portion exhibits a respective distinct varying characteristic modulation which when viewed by a human user induces a neural response that encodes the modulation.

When, as in (b), the user merely views the display location of the compound visual stimulus 706 (i.e. the location of display object 704), the induced neural response from each of the portions is balanced (illustrated by showing both portions at the same level of opacity). Although not shown here, the exploration currently focusing on display object 704 may optionally be shown (i.e. first validation) by displaying a feedback element such as a "crosshair" symbol at or near the display object 704. In certain embodiments, visual properties of the feedback element—e.g. scale—can be mapped to the real-time attention-level estimates of the neural decoder in order to close the neurofeedback loop.

Figure 7B:
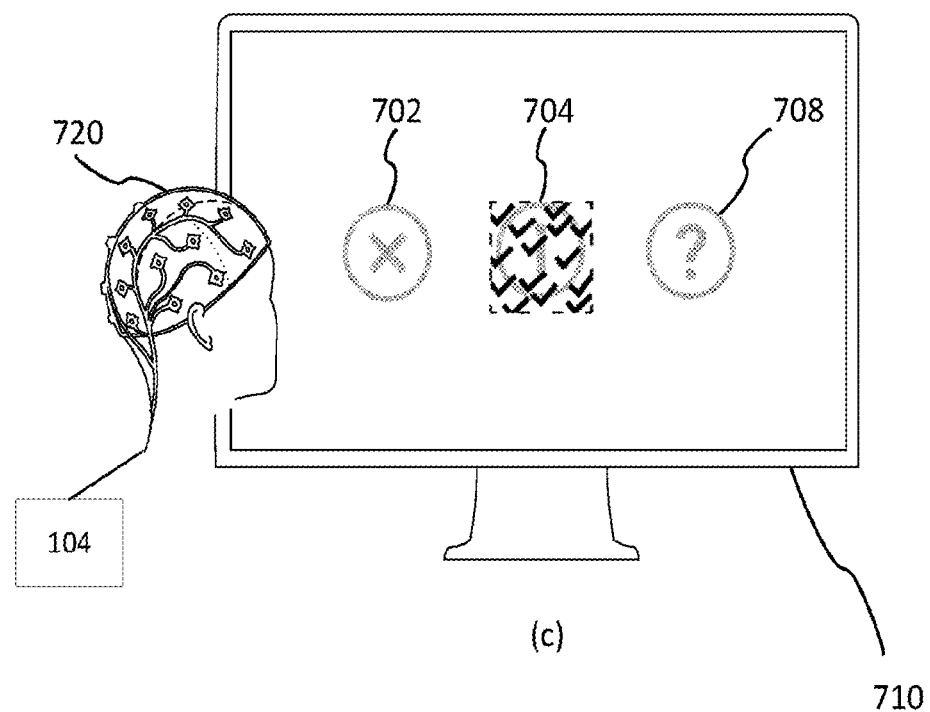
Figure 7B:
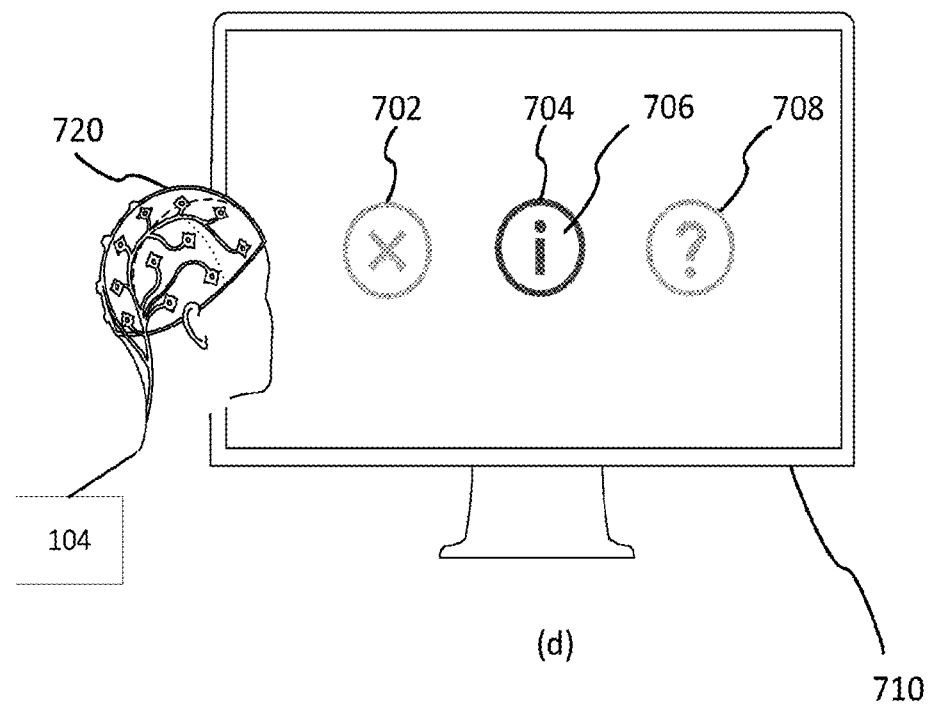

FIG. 7B continues the illustration of the user experience above. In (c), the user is now deliberately concentrating attention on the tick portion 502 (here, a validating stimulus)—depicted by showing only the tick portion 502, the cross portion ("balancing stimulus") being visually de-emphasized.

Optionally, a further feedback element may be displayed to confirm the valid selection of the display object 704—here, represented by the emphasized appearance of that object in (d).

In each of the embodiments above, the modulation may be applied preferentially or exclusively to a high spatial frequency component of the projected overlay image (i.e. the background and/or feedback element). Preferential modulation of HSF components of overlay objects, target objects and/or visual feedback elements may be used to improve the accuracy of determinations of objects of focus (and to reduce distraction effects).

Using the above approach, real-time and accurate decoding of the user's focus becomes more practical. There remain obstacles to performance: not least the potential for interference between respective stimuli presented in the same display. The stimulus at one display location may fall within the peripheral vision of a user viewing a second stimulus at a neighboring display location.

Figure 4:
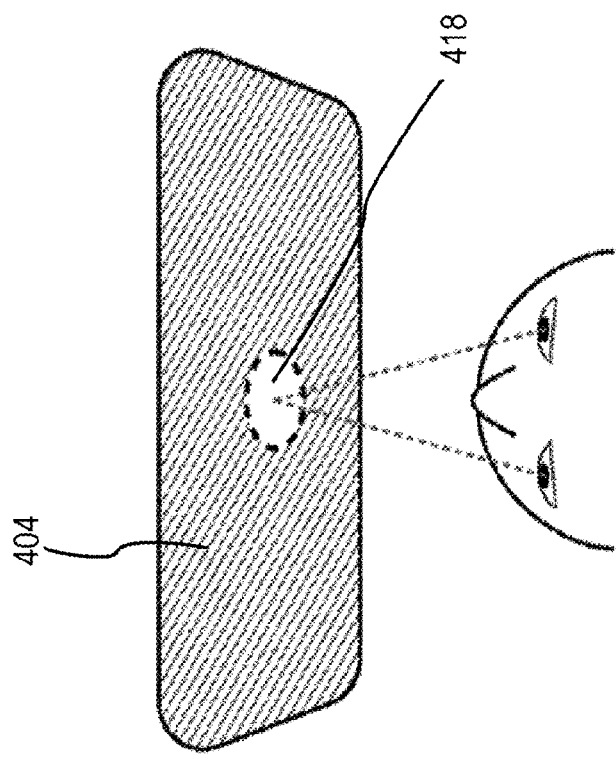
FIG. 4 illustrates a keypad use case for the BCI system of the present disclosure.
Figure 4:
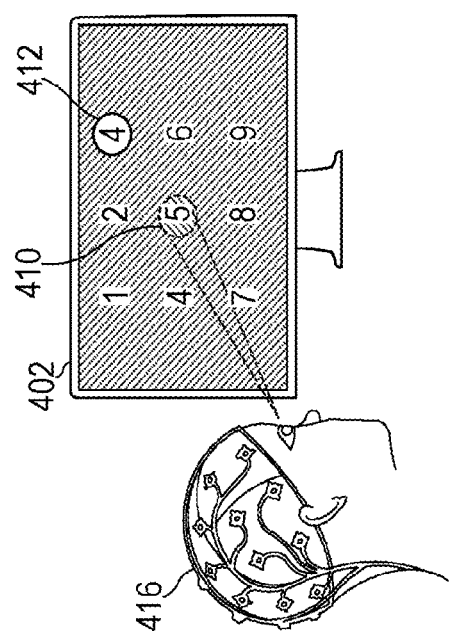

Returning to the keypad use case in FIG. 4, one may also observe the effects of peripheral vision on the BCI described above. The typical human visual system may be approximately considered as having a wide field of peripheral view 404 surrounding a narrower area 418 where the user's eyes focus. On the left hand side of FIG. 4, a subject 416 is shown viewing a display screen 402 displaying a plurality of digits 410, 412 in a keyboard. When the subject tries to focus on digit "5" 410, the other (i.e., peripheral) digits (such as "3", 412) act as distractors, drawing the user's attention momentarily, and induce interference in the user's visual system. This interference in turn impedes the performance of the BCI. For instance, when a user tries to focus on digit 5, the other (i.e., peripheral) digits act as distractors, drawing the user's attention momentarily, and induce interference in the user's visual system. This interference in turn impedes the performance of the BCI.

Co-pending International patent application number PCT/EP2020/081348, filed on Nov. 6, 2020, the entire specification of which is incorporated herein by reference, describes one approach to the challenge of determining the object of focus (the target) from the objects peripheral to the target (the distractors) with speed and accuracy. This approach relies upon characteristics of the human visual system.

Research into the way in which the human visual sensing operates has shown that, when peering at a screen with multiple objects and focusing on one of those objects, the human visual system will be receptive to both high spatial frequencies (HSF) and low spatial frequencies (LSF). Evidence shows that the human visual system is primarily sensitive to the HSF components of the specific display area being focused on (e.g. the object the user is staring at). For peripheral objects, conversely, the human visual system is primarily sensitive to their LSF components. In other words, the neural signals picked up will essentially be impacted by both the HSF components from the target under focus and the LSF components from the peripheral targets. However, since all objects evoke some proportion of both HSF and LSF, processing the neural signals to determine the focus object can be impeded by the LSF noise contributed by peripheral objects. This tends to make identifying the object of focus less accurate and less timely.

As the human visual system is tuned to process parallel multiple stimuli at different locations of the visual field, typically unconsciously, peripheral object stimuli will continue triggering neural responses in the users' brains, even if they appear in the periphery of the visual field. As a result, this poses competition among multiple stimuli and renders the specific neural decoding of the object of focus (the target) more difficult.

In PCT/EP2020/081348, a plurality of objects is displayed in such a way that each one is separated into a version composed only of the LSF components of the object and a version composed of only HSF components. The blinking visual stimulus used to elicit a decodable neural response is conveyed only through the HSF version of the object. The blinking HSF version is superimposed on the LSF version (which does not blink).

In certain embodiments, the BCI described above may be used in conjunction with real world objects, rendering the objects controllable or otherwise subject to interaction. In certain embodiments, the generation of stimuli is handled by one or more light source (such as a light emitting diode, LED) provided in association with (or even, on the surface of) the controllable object.

In certain embodiments, the generation of stimuli is handled by a projector or a scanning laser device so that visual stimuli are projected onto the controllable object and the controllable object outputs a visual stimulus by reflecting a projected stimulus.

As was the case in the BCI using a display screen through which the user interacts with on-screen objects, the controllable objects in the present disclosure can be made to exhibit visual stimuli with characteristic modulations (e.g. blinking stimuli) so that the neural response to the presence of those stimuli become evident and decodable from neural signals captured by a neural signal capture device (such as an EEG device).

In certain embodiments, the determination of focus of attention upon a visual display of a controllable device is used to address a command to that controllable object. The controllable object may then implement an action based on said command: for example, the controllable object may emit an audible sound, unlock a door, switch on or off, change an operational state, etc. The action may also provide the user with visual or other feedback associated with the controllable object: this may be used in conjunction with the positive feedback loop discussed above but may also provide a real-time indication of the valid selection of an operation associated with the controllable object.

Co-pending International patent application number PCT/EP2020/083088 filed on Nov. 23, 2020, the entire specification of which is incorporated herein by reference, describes how eye-tracking techniques may be used in conjunction with brain computer interfaces.

Figure 8:
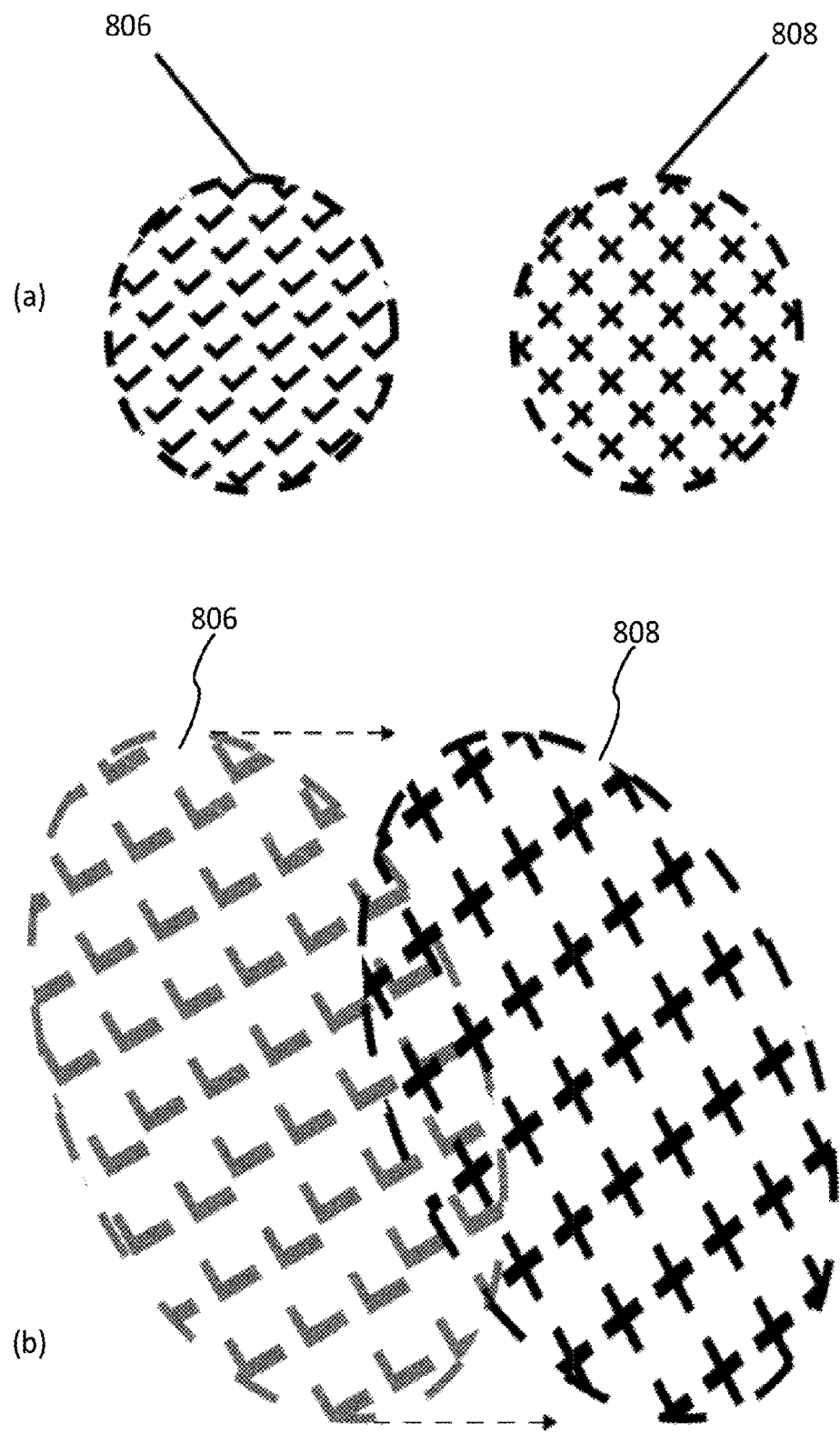
FIG. 8 illustrates a further exemplary embodiment of a compound visual stimulus in accordance with the present disclosure.

FIG. 8 illustrates an exemplary embodiment of compound visual stimulus in accordance with the present disclosure. Similar to the embodiment in FIG. 5A, the respective portions 806, 808 of a compound visual stimulus, each having a respective distinct varying characteristic modulation, are shown in (a). Again, respective portions may be visually distinguished by the user by color, movement, shape and/or orientation of stimuli component elements. In FIG. 8, the portions are shown as circular or oval patches, rather than the rectangular patches of FIGS. 5A and 5B. 'Tick' and 'cross' symbols are used in the respective portions of FIG. 8, but this is not to be understood as limiting since the reader will appreciate that any suitable mode of visual distinction might be adopted interchangeably.

Figure 9:
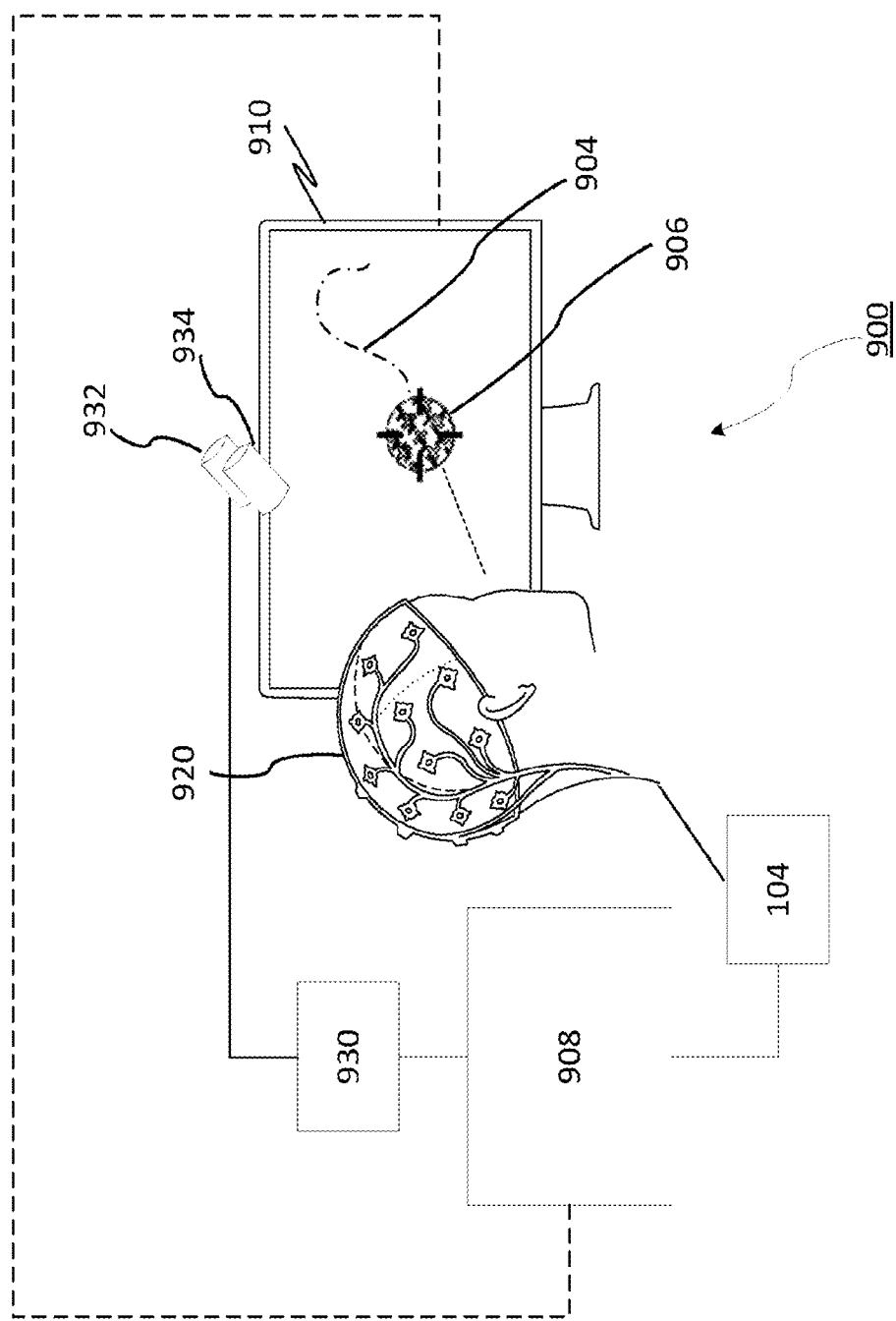
FIG. 9 illustrates the operation of an eye-tracking technology in conjunction with the BCI in accordance with the present disclosure.

FIG. 9 illustrates a system 900 combining an eye-tracking technology with the BCI in accordance with the present disclosure.

In the illustrated optical tracking technique, the output of respective eye tracking cameras 932, 934 is processed in an eye tracking unit 930. The eye tracking unit 930 outputs eye tracking information 904 including fixation information to a processing device 908. The processing device 908 (which may be the processing device 208 of FIG. 2) also receives neural signals detected at a neural response device 920 (e.g. the neural response device 206 of FIG. 2). As in FIG. 2, the processing device 908 executes instructions that interpret the received neural signals to determine feedback indicating the target object having the current focus of (visual) attention in real time. The processing device 908 also generates the image data presented on the display device 910 including at least one visual stimulus overlaying an object displayed on the display device 910, the visual stimulus being a compound visual stimulus in accordance with the present disclosure.

In certain embodiments, the compound visual stimulus is applied only to the object that is in the field of view, 906. The eye tracking information 904 may then be used to determine which object is in the field of view, while the compound visual stimulus (such as the stimulus illustrated in FIG. 8) may be used to determine a user's intention to validate one of the targets or not (and if so to validate the selection of that object) in accordance with the present disclosure.

Optionally, a further feedback element may be displayed to confirm the valid selection of the display object-represented, in FIG. 9, by the cross-hairs over the object in the field of view 906.

Eye tracking information typically indicates the angle of a notional point of gaze relative to fixed direction (such as a reference direction of the head). Conventional eye tracking techniques, even those using a camera for each of the user's eyes, generate information that is essentially two-dimensional-capable of discriminating points on a virtual sphere around the user's head but having difficulty capturing depth with any accuracy. Binocular eye tracking techniques are in development that attempt to resolve between different depths (i.e. distances from the user) using tracking information for more than one eye. Such techniques require considerable amounts of calibration to the particular user before they can be utilized with any reliability.

Figure 10:
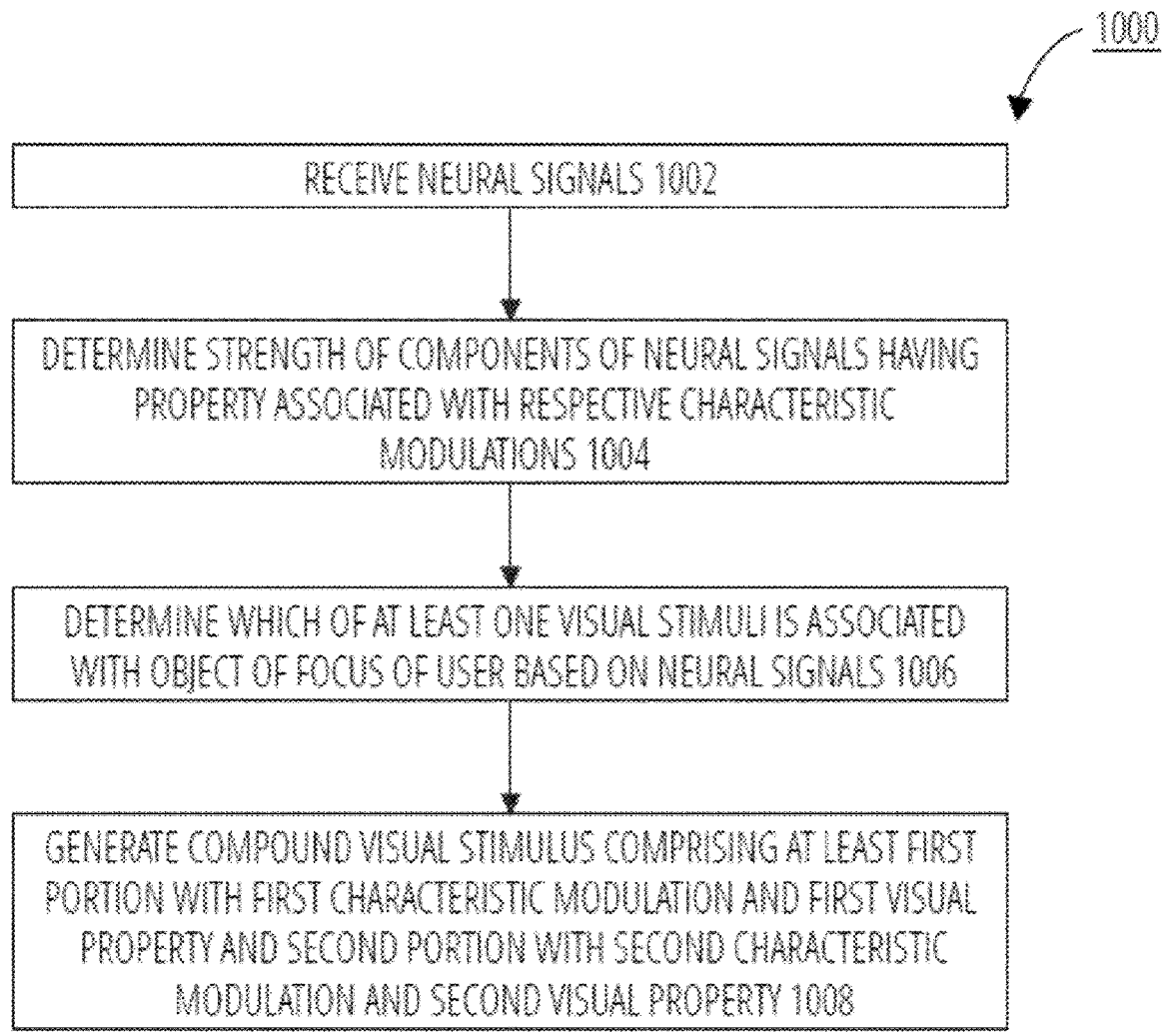
FIG. 10 illustrates the main functional blocks in the method of operation of the BCI in accordance with the present disclosure.

FIG. 10 illustrates the main functional blocks in the method of operation of a BCI system (for example, the BCI system illustrated in FIG. 2) in accordance with the present disclosure. The brain computer interface system includes a display unit, a stimulus generator and a neural signal capture device. The display unit displays image data including at least one object and outputs a visual stimulus to correspond to one or more of said objects, the visual stimulus having a characteristic modulation.

In block 1002, a hardware interfacing device (operatively coupled to the neural signal capture device and the stimulus generator), such as interface device 208, receives neural signals from the neural signal capture device.

In block 1004, the interfacing device determines a strength of components of the neural signals having a property associated with the respective characteristic modulations of the or each visual stimulus.

In block 1006, the interfacing device determines which of the at least one visual stimuli is associated with an object of focus of the user based on the neural signals, the object of focus being inferred from the presence and/or relative strength of the components of the neural signals having a property associated with the characteristic modulation of the visual stimulus.

In block 1008, the interfacing device causes the stimulus generator to generate the visual stimulus as a compound visual stimulus comprising at least a first portion with a first characteristic modulation and a first visual property and a second portion with a second characteristic modulation and a second visual property, the second visual property being distinct from the first visual property.

The active feedback (or "neurofeedback") loop of certain embodiments of the present disclosure is associated with several benefits in terms of the user experience (UX) and neural decoding. The feedback stimulus presents the user with a convenient guide to their attention (i.e. an "attention grabber") at a specific location in the display screen, helping them remain focused on the object. For viewers having certain attention-related conditions and mild visual impairments, it has been observed that the presence of such feature assists the user in maintaining focus.

Furthermore, the user is given a task (i.e. causing the feedback stimulus to approach a fully decoded state, indicating "validation" of a selection). This too helps the user to attend to particular objects while suppressing peripheral distractors.

As the user is more focused using such feedback stimuli, it is observed that the user-specific model of stimulus reconstruction built in the initial or calibration phase of operation of the BCI is more accurate while being constructed more rapidly.

In subsequent operational phases, the use of feedback stimuli as described above leads to improved accuracy and speed increases for the real-time BCI applications.

Figure 11:
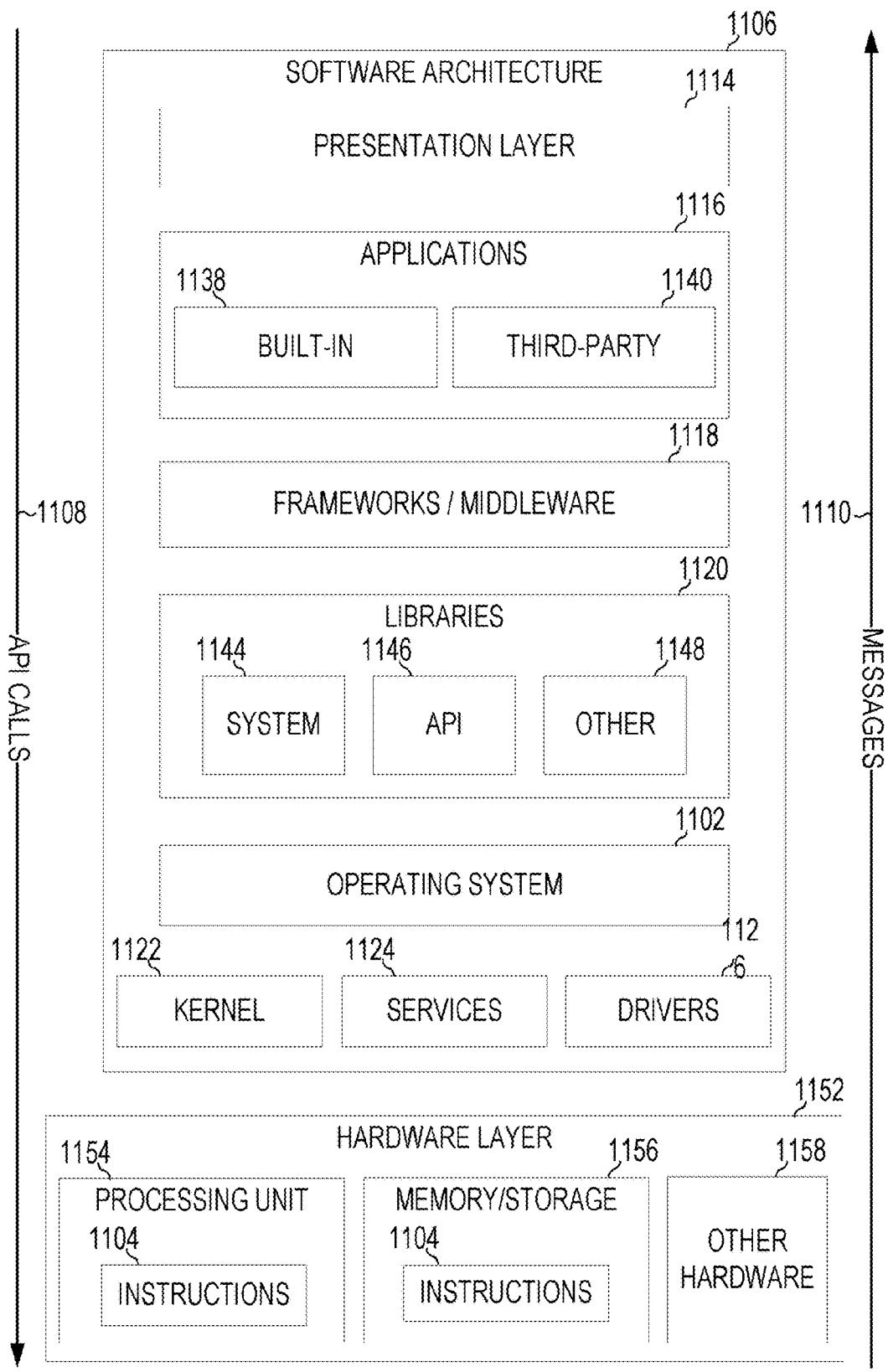
FIG. 11 is block diagram showing a software architecture within which the present disclosure may be implemented, in accordance with some example embodiments.

FIG. 11 is a block diagram illustrating an example software architecture 1106, which may be used in conjunction with various hardware architectures herein described. FIG. 11 is a non-limiting example of a software architecture and it will be appreciated that many other architectures may be implemented to facilitate the functionality described herein. The software architecture 1106 may execute on hardware such as machine 1200 of FIG. 12 that includes, among other things, processors 1204, memory 1206, and input/output (I/O) components 1218. A representative hardware layer 1152 is illustrated and can represent, for example, the machine 1200 of FIG. 12. The representative hardware layer 1152 includes a processing unit 1154 having associated executable instructions 1104. The executable instructions 1104 represent the executable instructions of the software architecture 1106, including implementation of the methods, modules and so forth described herein. The hardware layer 1152 also includes memory and/or storage modules shown as memory/storage 1156, which also have the executable instructions 1104. The hardware layer 1152 may also comprise other hardware 1158, for example dedicated hardware for interfacing with EEG electrodes, for interfacing with eye tracking units and/or for interfacing with display devices.

In the example architecture of FIG. 11, the software architecture 1106 may be conceptualized as a stack of layers where each layer provides particular functionality. For example, the software architecture 1106 may include layers such as an operating system 1102, libraries 1120, frameworks or middleware 1118, applications 1116 and a presentation layer 1114. Operationally, the applications 1116 and/or other components within the layers may invoke application programming interface (API) calls 1108 through the software stack and receive a response as messages 1110. The layers illustrated are representative in nature and not all software architectures have all layers. For example, some mobile or special purpose operating systems may not provide the frameworks/middleware 1118, while others may provide such a layer. Other software architectures may include additional or different layers.

The operating system 1102 may manage hardware resources and provide common services. The operating system 1102 may include, for example, a kernel 1122, services 1124, and drivers 1126. The kernel 1122 may act as an abstraction layer between the hardware and the other software layers. For example, the kernel 1122 may be responsible for memory management, processor management (e.g., scheduling), component management, networking, security settings, and so on. The services 1124 may provide other common services for the other software layers. The drivers 1126 may be responsible for controlling or interfacing with the underlying hardware. For instance, the drivers 1126 may include display drivers, EEG device drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1120 may provide a common infrastructure that may be used by the applications 1116 and/or other components and/or layers. The libraries 1120 typically provide functionality that allows other software modules to perform tasks in an easier fashion than by interfacing directly with the underlying operating system 1102 functionality (e.g., kernel 1122, services 1124, and/or drivers 1126). The libraries 1120 may include system libraries 1144 (e.g., C standard library) that may provide functions such as memory allocation functions, string manipulation functions, mathematic functions, and the like. In addition, the libraries 1120 may include API libraries 1146 such as media libraries (e.g., libraries to support presentation and manipulation of various media formats such as MPEG4, H.264, MP3, AAC, AMR, JPG, and PNG), graphics libraries (e.g., an OpenGL framework that may be used to render 2D and 3D graphic content on a display), database libraries (e.g., SQLite that may provide various relational database functions), web libraries (e.g., WebKit that may provide web browsing functionality), and the like. The libraries 1120 may also include a wide variety of other libraries 1148 to provide many other APIs to the applications 1116 and other software components/modules.

The frameworks 1118 (also sometimes referred to as middleware) provide a higher-level common infrastructure that may be used by the applications 1116 and/or other software components/modules. For example, the frameworks/middleware 1118 may provide various graphic user interface (GUI) functions, high-level resource management, high-level location services, and so forth. The frameworks/middleware 1118 may provide a broad spectrum of other APIs that may be used by the applications 1116 and/or other software components/modules, some of which may be specific to a particular operating system or platform.

The applications 1116 include built-in applications 1138 and/or third-party applications 1140.

The applications 1116 may use built-in operating system functions (e.g., kernel 1122, services 1124, and/or drivers 1126), libraries 1120, or frameworks/middleware 1118 to create user interfaces to interact with users of the system. Alternatively, or additionally, in some systems interactions with a user may occur through a presentation layer, such as the presentation layer 1114. In these systems, the application/module "logic" can be separated from the aspects of the application/module that interact with a user.

Figure 12:
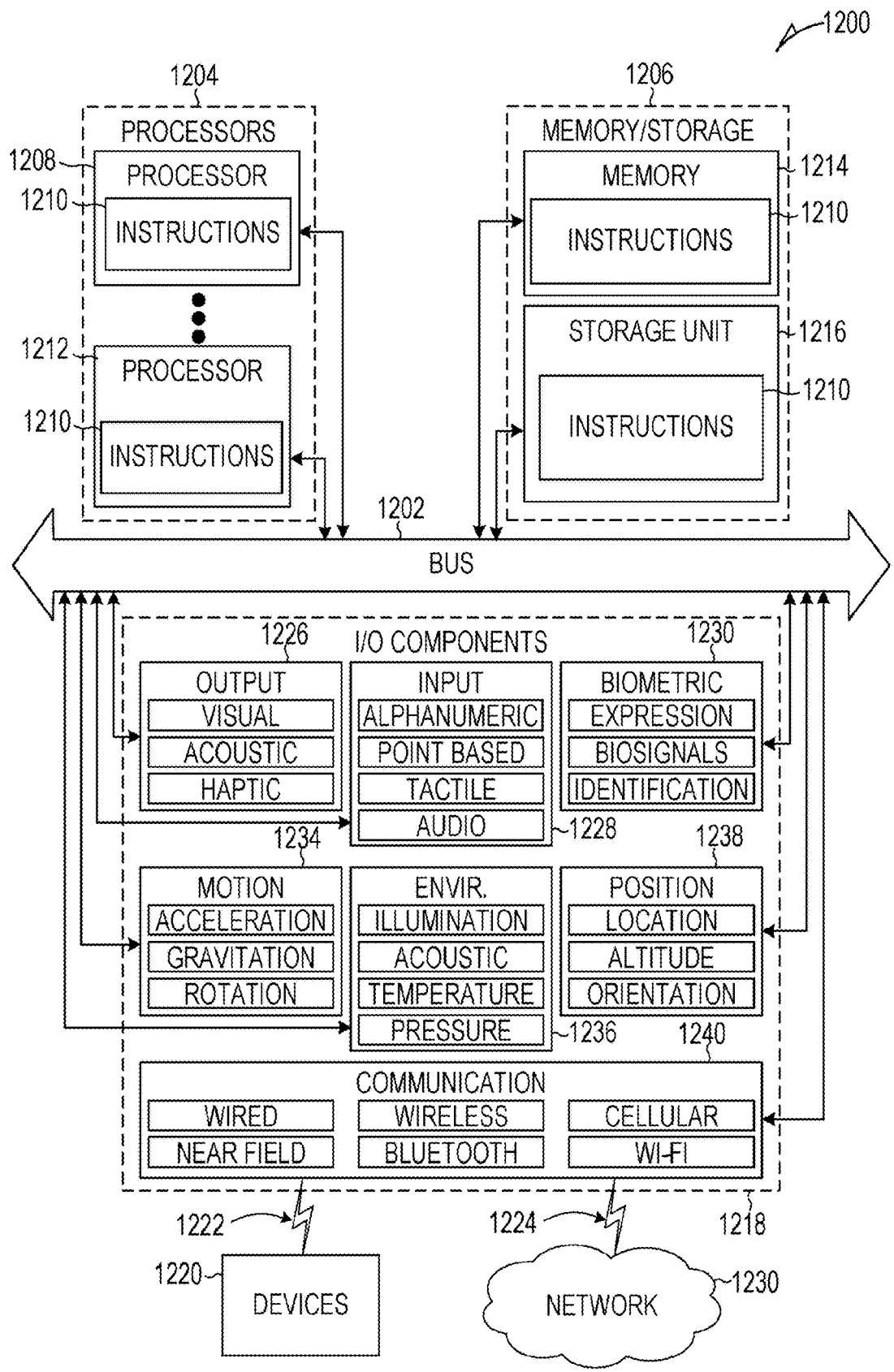
FIG. 12 is a diagrammatic representation of a machine, in the form of a computer system within which a set of instructions may be executed for causing the machine to perform any one or more of the methodologies discussed, in accordance with some example embodiments.

FIG. 12 is a block diagram illustrating components of a machine 1200, according to some example embodiments, able to read instructions from a machine-readable medium (e.g., a machine-readable storage medium) and perform any one or more of the methodologies discussed herein. Specifically, FIG. 12 shows a diagrammatic representation of the machine 1200 in the example form of a computer system, within which instructions 1210 (e.g., software, a program, an application, an applet, an app, or other executable code) for causing the machine 1200 to perform any one or more of the methodologies discussed herein may be executed. As such, the instructions 1210 may be used to implement modules or components described herein. The instructions 1210 transform the general, non-programmed machine 1200 into a particular machine programmed to carry out the described and illustrated functions in the manner described. In alternative embodiments, the machine 1200 operates as a standalone device or may be coupled (e.g., networked) to other machines. In a networked deployment, the machine 1200 may operate in the capacity of a server machine or a client machine in a server-client network environment, or as a peer machine in a peer-to-peer (or distributed) network environment. The machine 1200 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1210, sequentially or otherwise, that specify actions to be taken by the machine 1200. Further, while only a single machine 1200 is illustrated, the term "machine" shall also be taken to include a collection of machines that individually or jointly execute the instructions 1210 to perform any one or more of the methodologies discussed herein.

The machine 1200 may include processors 1204, memory 1206, and input/output (I/O) components 1218, which may be configured to communicate with each other such as via a bus 1202. In an example embodiment, the processors 1204 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1208 and a processor 1212 that may execute the instructions 1210. The term "processor" is intended to include multi-core processor that may comprise two or more independent processors (sometimes referred to as "cores") that may execute instructions contemporaneously. Although FIG. 12 shows multiple processors, the machine 1200 may include a single processor with a single core, a single processor with multiple cores (e.g., a multi-core processor), multiple processors with a single core, multiple processors with multiples cores, or any combination thereof.

The memory 1206 may include a memory 1214, such as a main memory, a static memory, or other memory storage, and a storage unit 1216, both accessible to the processors 1204 such as via the bus 1202. The storage unit 1216 and memory 1214 store the instructions 1210 embodying any one or more of the methodologies or functions described herein. The instructions 1210 may also reside, completely or partially, within the memory 1214, within the storage unit 1216, within at least one of the processors 1204 (e.g., within the processor's cache memory), or any suitable combination thereof, during execution thereof by the machine 1200. Accordingly, the memory 1214, the storage unit 1216, and the memory of processors 1204 are examples of machine-readable media.

As used herein, "machine-readable medium" means a device able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)), and/or any suitable combination thereof. The term "machine-readable medium" should be taken to include a single medium or multiple media (e.g., a centralized or distributed database, or associated caches and servers) able to store the instructions 1210. The term "machine-readable medium" shall also be taken to include any medium, or combination of multiple media, that is capable of storing instructions (e.g., instructions 1210) for execution by a machine (e.g., machine 1200), such that the instructions, when executed by one or more processors of the machine 1200 (e.g., processors 1204), cause the machine 1200 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The input/output (I/O) components 1218 may include a wide variety of components to receive input, provide output, produce output, transmit information, exchange information, capture measurements, and so on. The specific input/output (I/O) components 1218 that are included in a particular machine will depend on the type of machine. For example, user interface machines and portable machines such as mobile phones will likely include a touch input device or other such input mechanisms, while a headless server machine will likely not include such a touch input device. It will be appreciated that the input/output (I/O) components 1218 may include many other components that are not shown in FIG. 12.

The input/output (I/O) components 1218 are grouped according to functionality merely for simplifying the following discussion and the grouping is in no way limiting. In various example embodiments, the input/output (I/O) components 1218 may include output components 1226 and input components 1228. The output components 1226 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1228 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instruments), tactile input components (e.g., a physical button, a touch screen that provides location and/or force of touches or touch gestures, or other tactile input components), audio input components (e.g., a microphone), and the like.

In further example embodiments, the input/output (I/O) components 1218 may include biometric components 1230, motion components 1234, environment components 1236, or position components 1238 among a wide array of other components. For example, the biometric components 1230 may include components to detect expressions (e.g., hand expressions, facial expressions, vocal expressions, body gestures, or eye tracking), measure biosignals (e.g., blood pressure, heart rate, body temperature, perspiration, or brain waves, such as the output from an EEG device), identify a person (e.g., voice identification, retinal identification, facial identification, fingerprint identification, or electroencephalogram based identification), and the like. The motion components 1234 may include acceleration sensor components (e.g., accelerometer), gravitation sensor components, rotation sensor components (e.g., gyroscope), and so forth. The environmental environment components 1236 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 1238 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The input/output (I/O) components 1218 may include communication components 1240 operable to couple the machine 1200 to a network 1232 or devices 1220 via a coupling 1224 and a coupling 1222 respectively. For example, the communication components 1240 may include a network interface component or other suitable device to interface with the network 1232. In further examples, communication components 1240 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1220 may be another machine or any of a wide variety of peripheral devices (e.g., a peripheral device coupled via a Universal Serial Bus (USB)). Where an EEG device, an eye tracking unit or a display device is not integral with the machine 1200, the device 1220 may be an EEG device, an eye tracking unit and/or a display device.

Although described through a number of detailed exemplary embodiments, the portable devices for the acquisition of electroencephalographic signals according to the present disclosure comprise various variants, modifications and improvements which will be obvious to those skilled in the art, it being understood that these various variants, modifications and improvements fall within the scope of the subject of the present disclosure, as defined by the following claims.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Thus, the present disclosure describes a system and method for improving the accuracy, speed performance and visual comfort of BCIs.

EXAMPLES

To better illustrate the system and methods disclosed herein, a non-limiting list of examples is provided here:

1. A brain computer interface system, comprising:
    a display unit for displaying image data, the image data including at least one object, the display unit further outputting a respective visual stimulus to correspond to one or more of said objects,
    a stimulus generator for generating the or each visual stimulus with a corresponding characteristic modulation;
    a neural signal capture device configured to capture neural signals associated with a user; and
    an interfacing device operatively coupled to the neural signal capture device and the stimulus generator, the interfacing device being configured to:
        receive the neural signals from the neural signal capture device;
        determine a strength of components of the neural signals having a property associated with the respective characteristic modulations of the or each visual stimulus;
        determine which of the at least one visual stimuli is associated with an object of focus of the user based on the neural signals, the object of focus being inferred from the presence and/or relative strength of the components of the neural signals having a property associated with the characteristic modulation of the visual stimulus; and
        cause the stimulus generator to generate the visual stimulus as a compound visual stimulus comprising at least a first portion with a first characteristic modulation and a first visual property and a second portion with a second characteristic modulation and a second visual property, the second visual property being distinct from the first visual property.
2. The system of example 1, wherein the modulation is selectively applied to the high spatial frequency (HSF) component of the visual stimulus.
3. A method of operation of a brain computer interface system, the brain computer interface system including a display unit, a stimulus generator and a neural signal capture device, the display unit displaying image data including at least one object and outputting a visual stimulus to correspond to one or more of said objects, the visual stimulus having a characteristic modulation, wherein the method comprises, in a hardware interfacing device operatively coupled to the neural signal capture device and the stimulus generator:

receiving the neural signals from the neural signal capture device;

determining a strength of components of the neural signals having a property associated with the respective characteristic modulations of the or each visual stimulus;

determining which of the at least one visual stimuli is associated with an object of focus of the user based on the neural signals, the object of focus being inferred from the presence and/or relative strength of the components of the neural signals having a property associated with the characteristic modulation of the visual stimulus; and causing the stimulus generator to generate the visual stimulus as a compound visual stimulus comprising at least a first portion with a first characteristic modulation and a first visual property and a second portion with a second characteristic modulation and a second visual property, the second visual property being distinct from the first visual property.

4. The method of example 3, wherein the modulation is selectively applied to the high spatial frequency (HSF) component of the visual stimulus.

5. A computer-readable storage medium for a brain computer interface system, the brain computer interface system including a display unit, a stimulus generator and a neural signal capture device, the display unit displaying image data including at least one object and outputting a visual stimulus to correspond to one or more of said objects, the visual stimulus having a characteristic modulation, wherein the computer-readable storage medium carries instructions that, when executed by a computer operatively coupled to the neural signal capture device and the stimulus generator, cause the computer to perform operations comprising:

receiving the neural signals from the neural signal capture device;

determining a strength of components of the neural signals having a property associated with the respective characteristic modulations of the or each visual stimulus;

determining which of the at least one visual stimuli is associated with an object of focus of the user based on the neural signals, the object of focus being inferred from the presence and/or relative strength of the components of the neural signals having a property associated with the characteristic modulation of the visual stimulus; and causing the stimulus generator to generate the visual stimulus as a compound visual stimulus comprising at least a first portion with a first characteristic modulation and a first visual property and a second portion with a second characteristic modulation and a second visual property, the second visual property being distinct from the first visual property.

What is claimed is:

1. A method comprising:

generating a compound visual stimulus with multiple distinguishable portions;

displaying the compound visual stimulus to a user;

utilizing a first decoding model to determine first decoded neural signals captured from the user in response to a first portion of the compound visual stimulus;

utilizing a second decoding model to decode second decoded neural signals captured from the user in response to a second portion of the compound visual stimulus;

comparing the first decoded neural signals and the second decoded neural signals to assess the attentional engagement of the user; and determining an attention of the user as defocused based on a balanced response to the first portion and the second portion of the compound visual stimulus.

2. The method of claim 1, further comprising:

receiving images captured by at least one eye tracking camera and determining eye-tracking information according to the captured image, wherein determining the attention of the user as defocused further includes using the eye-tracking information.

3. The method of claim 2, wherein the eye-tracking information includes at least one of a direction of gaze and a depth of focus.

4. The method of claim 1, wherein a modulation is selectively applied to the multiple distinguishable portions of the compound visual stimulus.

5. The method of claim 4, wherein the modulation is applied to a high spatial frequency (HSF) component of the compound visual stimulus.

6. The method of claim 1, wherein a color is selectively applied to the multiple distinguishable portions of the compound visual stimulus.

7. The method of claim 1, wherein a motion is selectively applied to the multiple distinguishable portions of the compound visual stimulus.

8. A machine comprising:

at least one processor; and at least one memory storing instructions that, when executed by the at least one processor, cause the machine to perform operations comprising:

generating a compound visual stimulus with multiple distinguishable portions;

displaying the compound visual stimulus to a user;

utilizing a first decoding model to determine first decoded neural signals captured from the user in response to a first portion of the compound visual stimulus;

utilizing a second decoding model to decode second decoded neural signals captured from the user in response to a second portion of the compound visual stimulus;

comparing the first decoded neural signals and the second decoded neural signals to assess the attentional engagement of the user; and determining an attention of the user as defocused based on a balanced response to the first portion and the second portion of the compound visual stimulus.

9. The machine of claim 8, wherein the operations further comprise:

receiving images captured by at least one eye tracking camera and determining eye-tracking information according to the captured image, wherein determining the attention of the user as defocused further includes using the eye-tracking information.

10. The machine of claim 9, wherein the eye-tracking information includes at least one of a direction of gaze and a depth of focus.

11. The machine of claim 8, wherein a modulation is selectively applied to the multiple distinguishable portions of the compound visual stimulus.

12. The machine of claim 11, wherein the modulation is applied to a high spatial frequency (HSF) component of the compound visual stimulus.

13. The machine of claim 8, wherein a color is selectively applied to the multiple distinguishable portions of the compound visual stimulus.

14. The machine of claim 8, wherein a motion is selectively applied to the multiple distinguishable portions of the compound visual stimulus.

15. A machine-readable medium, the machine-storage medium including instructions that, when executed by a machine, cause the machine to perform operations comprising:
   generating a compound visual stimulus with multiple distinguishable portions;
   displaying the compound visual stimulus to a user;
   utilizing a first decoding model to determine first decoded neural signals captured from the user in response to a first portion of the compound visual stimulus;
   utilizing a second decoding model to decode second decoded neural signals captured from the user in response to a second portion of the compound visual stimulus;
   comparing the first decoded neural signals and the second decoded neural signals to assess the attentional engagement of the user; and
   determining an attention of the user as defocused based on a balanced response to the first portion and the second portion of the compound visual stimulus.

16. The machine-readable medium of claim 15, wherein the operations further comprise:
   receiving images captured by at least one eye tracking camera and determining eye-tracking information according to the captured image,
   wherein determining the attention of the user as defocused further includes using the eye-tracking information.

17. The machine-readable medium of claim 16, wherein the eye-tracking information includes at least one of a direction of gaze and a depth of focus.

18. The machine-readable medium of claim 15, wherein a modulation is selectively applied to the multiple distinguishable portions of the compound visual stimulus.

19. The machine-readable medium of claim 18, wherein the modulation is applied to a high spatial frequency (HSF) component of the compound visual stimulus.

20. The machine-readable medium of claim 15, wherein a color is selectively applied to the multiple distinguishable portions of the compound visual stimulus.

* * * * *